US009980921B2

(12) United States Patent
Kao et al.

(10) Patent No.: US 9,980,921 B2
(45) Date of Patent: May 29, 2018

(54) TRANSDERMAL DELIVERY SYSTEM CONTAINING METHYLPHENIDATE OR ITS SALTS AND METHODS THEREOF

(71) Applicant: TAHO Pharmaceuticals Ltd., Taipei (TW)

(72) Inventors: Shen-Yung Kao, New Taipei (TW); Taijung Wu, New Taipei (TW); Catherine Lee, West Linn, OR (US)

(73) Assignee: TAHO PHARMACEUTICALS LTD., Taipei (TW)

( * ) Notice: Subject to any disclaimer, the term of this patent is extended or adjusted under 35 U.S.C. 154(b) by 0 days. days.

(21) Appl. No.: 15/634,188

(22) Filed: Jun. 27, 2017

(65) Prior Publication Data

US 2018/0000746 A1 Jan. 4, 2018

Related U.S. Application Data

(60) Provisional application No. 62/357,316, filed on Jun. 30, 2016.

(51) Int. Cl.
*A61K 9/70* (2006.01)
*A61K 9/00* (2006.01)
*A61K 31/4458* (2006.01)
*A61K 47/32* (2006.01)
*C08F 230/08* (2006.01)

(52) U.S. Cl.
CPC .......... *A61K 9/7084* (2013.01); *A61K 9/0014* (2013.01); *A61K 31/4458* (2013.01); *A61K 47/32* (2013.01); *C08F 230/08* (2013.01)

(58) Field of Classification Search
CPC ................ A61K 9/0014; A61K 9/7084; A61K 31/4458; A61K 47/32; C08F 230/08
See application file for complete search history.

(56) References Cited

U.S. PATENT DOCUMENTS

| | | | |
|---|---|---|---|
| 2005/0019385 A1 | 1/2005 | Houze | |
| 2006/0078602 A1 | 4/2006 | Kanios | |
| 2011/0200663 A1 | 8/2011 | Hara et al. | |
| 2013/0324575 A1 | 12/2013 | Mantelle et al. | |
| 2014/0271792 A1* | 9/2014 | Liao .................. | A61K 31/4458 424/443 |
| 2016/0030362 A1 | 2/2016 | Liao et al. | |
| 2016/0113908 A1 | 4/2016 | Deshmukh et al. | |

OTHER PUBLICATIONS

Carmen Cheng, et al., Chemical Leukoderma Associated with Methylphenidate Transdermal System: Data From the US Food and Drug Administration Adverse Event Reporting System, The Journal of Pediatrics, Jan. 2017, vol. 180, pp. 241-246.
(Continued)

*Primary Examiner* — Michael B. Pallay
(74) *Attorney, Agent, or Firm* — Leason Ellis LLP

(57) ABSTRACT

Disclosed herein is a transdermal delivery system comprising methylphenidate or its salt as an active ingredient. Also provided are methods of delivering a therapeutically effective amount of methylphenidate to a subject for the treatment of a disease condition. The disease condition includes a neurological condition such as Attention Deficit Disorder (ADD) and/or Attention Deficit/Hyperactivity Disorder (ADHD). Kits including the transdermal delivery system and methods of making and using the transdermal delivery system are also provided.

25 Claims, 8 Drawing Sheets

(56) References Cited

OTHER PUBLICATIONS

Robert L. Findling, et al., Transdermal Therapy for Attention-Deficit Hyperactivity Disorder with the Methylphenidate Patch (MTS), CNS Drugs (2014), 28: pp. 217-228.
Chemistry Reviews: Sherita D. McLamore, Ph.D., et al, Center and Drug Evaluation and Research, Methypatch (Methyphenidate Transdermal System), Noven Pharmaceuticals, Inc. Review date: Dec. 14, 2005; Application No. 21-514.
International Search Report and Written Opinion in corresponding PCT Application No. PCT/US17/39650, dated Oct. 5, 2017.

* cited by examiner

TRANSDERMAL DELIVERY SYSTEM CONTAINING METHYLPHENIDATE OR ITS SALTS AND METHODS THEREOF

RELATED APPLICATION

This application claims the benefit of U.S. provisional application Ser. No. 62/357,316, filed Jun. 30, 2016, which is hereby incorporated by reference in its entirety.

1. INTRODUCTION

Disclosed herein is a transdermal delivery system comprising methylphenidate or its pharmaceutically acceptable salt as an active ingredient. Also provided are methods of delivering a therapeutically effective amount of methylphenidate to a subject for the treatment of a disease condition. The disease condition includes a neurological condition such as Attention Deficit Disorder (ADD) and/or Attention Deficit/Hyperactivity Disorder (ADHD). Kits including the transdermal delivery system and methods of making and using such delivery system are also provided.

2. BACKGROUND

It has been reported that ADD and/or ADHD are developmental disorders that consists of attention span, impulse control and self-control. It has been reported that though the pathogenesis of ADD and/or ADHD has not been fully investigated, it is known that traditionally, methylphenidate has been used in the treatment of ADD and/or ADHD for both children and adults. It is also known that methylphenidate can also be used in the treatment of diseases including but not limited to postural orthostatic tachycardia syndrome and narcolepsy.

Daytrana® (methylphenidate transdermal system) is available in four dosage strengths (10, 15, 20 and 30 mg/day) and is applied for 9 hours using patch sizes correlated with the dose (12.5, 18.75, 25 and 37.5 cm2, respectively). Daytrana® is a polymer matrix comprising an acrylic pressure-sensitive adhesive. However, the peel force from the release liner of the patch increases over time. This creates a serious issue as patients may encounter difficulties or unable to remove the release liner for use. In addition, it has been reported that currently available methylphenidate patches have leaking issues where the methylphenidate leaks out of the patch. This also creates a problem where the large size patches are too soft to handle. This problem is more severe if the methylphenidate patches are stored for several months or longer. See US20140271792 A1, US 2016/0030362 A1 and NDA 21-514 CMC review. In addition, currently available methylphenidate patches have low permeation and flux rate (~9.1 µg/cm2 hr see US 2016/0030362 A1). As methylphenidate will cause skin sensitization (Daytrana® package insert, Cheng C. J of Pediatrics January 2017 Vol 180, P 241-246), when compensate for the low permeation rate, larger patches are needed, i.e. 37.5 cm$^2$.

Therefore, there is a need to develop an optimal methylphenidate formulation with high flux to reduce drug loading and patch size to minimize the skin sensitization and exhibit suitable physical and pharmacokinetic properties. The presently disclosed transdermal delivery system has a higher permeation and flux rate than previously known methylphenidate transdermal delivery system in the market. Because of these improved properties, the same or more of the active pharmaceutical agents can be delivered. The patches of the present disclosure do not have the currently undesirable issues for being leaky, too soft to handle and too large to be comfortably applied to a patient. The presently disclosed methylphenidate transdermal delivery system improves the quality of life of caregivers and patients who are suffering from ADD and/or ADHD, postural orthostatic tachycardia syndrome and narcolepsy (Findling R, Dinh S, CNS Drugs (2014) 28:217-228).

3. SUMMARY

It is discovered that a transdermal delivery system comprising: (i) a silicone layer; (ii) a drug-containing matrix layer that comprises: (a) methylphenidate or its pharmaceutically acceptable salt; and (b) a rubber based polymer comprising a tackifier, has improved permeation and flux over the current methylphenidate transdermal delivery system in the market by about 60%-70%. This dramatic increase in permeation and flux of the presently disclosed methylphenidate transdermal delivery system provide superior improvements to the lives of the patients.

An object of the present disclosure is to provide a method and a system for transdermal delivery of methylphenidate or its salt as an active ingredient to a subject through skin or other body surface.

The transdermal delivery system comprises a backing layer, a silicone layer, a drug-containing matrix layer, and a release liner. The system can be applied to the skin or the mucosa of a subject over an extended period of time without side effects.

In one embodiment, the transdermal delivery system comprises: (a) a silicon adhesive layer; and (b) a rubber-based polymer that comprises a hydrogenated synthetic hydrocarbon tackifier has the following properties: (i) exhibits good adherence to skin; (ii) ability to be peeled or removed without substantial trauma to the skin; (iii) retention of tackiness over time. In one embodiment, the release liner can be removed from the presently disclosed transdermal delivery system without losing the drug-containing matrix to the release liner. In one embodiment, the transdermal delivery system does not suffer from peel release problems associated with other methylphenidate transdermal delivery system. In one embodiment, the transdermal delivery system has a lower residual drug content after application than a transdermal delivery system that does not comprise a silicone adhesive layer. The presence of a silicon adhesive layer between the backing layer and the drug-containing matrix layer improves permeation of the drugs from the transdermal system to the subject.

Also disclosed is a transdermal system having improved drug loading with desirable tack and adhesion. In one embodiment, the transdermal system comprises an adhesive. In one embodiment, the transdermal system comprises more than one type of copolymer in the drug-containing matrix layer.

In one embodiment, the methylphenidate transdermal delivery system of the present disclosure comprises methylphenidate as the active pharmaceutical ingredient which may be in free base form or a pharmaceutically acceptable salt thereof. In one embodiment, the methylphenidate transdermal delivery system further comprises a rubber-based polymer comprising a tackifier for providing adhesive property. In one embodiment, the rubber-based polymer comprises styrene-butadiene block copolymer rubber. In one embodiment, the styrene-butadiene block copolymer rubber comprises a hydrogenated synthetic hydrocarbon tackifier. In one embodiment, the methylphenidate transdermal delivery system further comprises one or more excipients. In one embodiment, the silicone adhesive layer provides an increased flux. In one embodiment, the transdermal delivery system increased flux of methylphenidate from the transdermal delivery system to the user's skin by lowering solubility of the methylphenidate or its pharmaceutically acceptable salt in the transdermal delivery system relative to the solubility of the methylphenidate or its pharmaceutically acceptable salt in the stratum corneum layer of the user's skin.

Importantly, while capable of improving the flux, the one or more excipients would preferably not affect the stability of the transdermal delivery system. Specifically, since methylphenidate is reactive with substances such as bases, water and oxidants, the one or more excipients should not be, nor contain substances that degrade methylphenidate. Therefore, the one or more excipients preferably are not, does not contain nor does not attract base, water, oxidant and/or any substances that may degrade methylphenidate, but are found to substantially increase flux. In an embodiment, the one or more excipients comprise one or more saturated carbohydrates. More specifically, in certain embodiments, the one or more excipients comprise squalane, isosqualane, monocyclosqualane, hemisqualane, sesquisqualane, squalene and/or cyclomethicone.

In certain embodiments, more than one excipients are combined in order to optimize the flux while not detrimentally affecting the stability of the transdermal delivery system.

In an embodiment, the methylphenidate transdermal delivery system comprises methylphenidate free base, styrene-butadiene block copolymer rubber wherein the methylphenidate free base comprises about 5% to about 20% by total weight, styrene-butadiene block copolymer rubber comprises about 70% to about 90% by total weight.

In order to lend adhesive property to the composition, in one embodiment, the methylphenidate transdermal delivery system further comprises a tackifier. In one embodiment, the drug-containing matrix does not contain any added tackifier. In addition, in order to increase stability of the transdermal delivery system, in one embodiment, the transdermal delivery system further comprises an antioxidant. In one embodiment, the methyophenidate transdermal delivery system further comprises one or more permeation enhancers in addition to the one or more excipients.

In certain embodiments, the drug transdermal delivery system comprises a matrix which comprises methylphenidate or its salt dispersed therein. In certain embodiments, the system and method include a matrix formed of a polymer and methylphenidate or its salt dispersed uniformly within the polymer.

In one embodiment, provided herein is a transdermal delivery system which comprises: (i) a backing layer; (ii) a silicone adhesive layer; (iii) a drug-containing matrix layer comprising methylphenidate or its pharmaceutically acceptable salt, styrene-butadiene block copolymer rubber and hydrogenated synthetic hydrocarbon tackifier; and (iv) a release liner.

In certain embodiments, the methylphenidate or its pharmaceutically acceptable salt is about 5 to about 30% by weight based on the total weight of the drug-containing matrix layer. In certain embodiments, the methylphenidate or its pharmaceutically acceptable salt is about 8, about 12, about 14 or about 20% by weight based on the total weight of the drug-containing matrix layer. In certain embodiments, the first layer comprises about 75-78%, 78-80%, 80-90%, 90-100% by weight of silicone. In certain embodiments, the styrene-butadiene block copolymer rubber and hydrogenated synthetic hydrocarbon tackifier is about 70-80%, 80-95% by weight based on the total weight of the drug containing matrix layer.

In certain embodiments, the silicone adhesive layer has a thickness from about 20 μm to about 60 μm.

In certain embodiments, the drug-containing matrix layer has a thickness from about 20 μm to about 60 μm. In certain embodiments, the system has a flux of about 10-44 μg/cm$^2$ hr. In certain embodiments, the methylphenidate or its pharmaceutically acceptable salt is about 8-20) % by weight of the drug-containing matrix layer.

In one embodiment, the present disclosed transdermal delivery system achieves high flux in a system with a smaller active surface area as compared to other methylphenidate transdermal delivery system. In one embodiment, the transdermal delivery system has a unit size having a dimension of less than 40 cm$^2$. The disclosed transdermal delivery system offers high advantages of cost savings and improved patient compliance.

In one embodiment, the transdermal delivery system releases at least about 80% methylphenidate within 12 hours in an in vitro dissolution media at about pH1.2.

While the actual flux may vary, in certain embodiments, the skin permeation rates are about 3-4 μg/cm$^2$/hr, about 4-5 μg/cm$^2$/hr, about 5-6 μg/cm$^2$/hr, about 6-7 μg/cm$^2$/hr, about 7-8 μg/cm$^2$/hr, about 8-9 μg/cm$^2$/hr, about 9-10 μg/cm$^2$/hr, about 10-11 μg/cm$^2$/hr, or about 11-12 μg/cm$^2$/hr, about 12-15 μg/cm$^2$/hr, about 15-20 μg/cm$^2$/hr, about 20-25 μg/cm$^2$/hr, about 25-30 μg/cm$^2$/hr, about 30-35 μg/cm$^2$/hr, about 35-40 μg/cm$^2$/hr, about 40-45 μg/cm$^2$/hr, or about 45-50 μg/cm$^2$/hr.

In certain embodiments, the flux is about 13-44 μg/cm$^2$ hr.

In certain embodiments, the transdermal delivery systems are formulated to provide a cumulative delivered amount (also referred to herein as cumulative flux) of the active agent to a subject when the formulation is applied to the skin of a subject for an extended period of time as described infra. In certain embodiments, the transdermal formulations are configured to provide a cumulative delivered amount of the active agent of about 1-100 μg/cm$^2$, about 100-150 μg/cm$^2$, about 150-200 μg/cm$^2$, about 200-250 μg/cm$^2$, about 250-300 μg/cm$^2$, about 300-350 μg/cm$^2$, about 350-400 μg/cm$^2$, about 400-450 μg/cm$^2$, about 450-500 μg/cm$^2$, about 500-550 μg/cm$^2$, about 550-600 μg/cm$^2$, about 600-650 μg/cm$^2$, about 650-700 μg/cm$^2$, about 700-750 μg/cm$^2$, 750 m-800 μg/cm$^2$, 800-850 μg/cm2, about 850-900 μg/cm$^2$, about 900-950 μg/cm$^2$, or about 950-1000 μg/cm$^2$.

The size (i.e., area) of the transdermal delivery system may vary, but is within a range of the active agent to the subject. It is also important that the subject wearing the transdermal delivery system finds the system to be easy to apply and comfortable to use for a period of time so as to improve compliance. In certain embodiments, the size of the formulation is chosen in view of the desired transdermal flux rate of the active agent and the target dosage. In certain embodiments, the transdermal delivery system has a size that is about 2-6 cm$^2$, about 6-10 cm$^2$, about 10-20 cm$^2$, about 20-30 cm$^2$, about 30-40 cm$^2$, about 40-50 cm$^2$, about 50-100 cm$^2$, about 100-130 cm$^2$, about 130-140 cm$^2$, about 140-150 cm$^2$ or about 150-200 cm$^2$.

The transdermal delivery system of the present disclosure is formulated to provide a therapeutically effective amount of the active agent to a subject when the topical patch is applied to a skin site of a subject for an extended period of time (e.g., a multi-day period of time). For example, the extended period of time may be a period of time that is about 6-12 hours, about 12-24 hours, about 1-2 days.

In certain embodiments, the AUC0-t, is about 80-120 h·ng/mL, 120-160 h·ng/mL, 160-200 h·ng/mL, 200-240 h·ng/mL, 240-280 h·ng/mL, 280-320 h·ng/mL, 320-360 h·ng/mL, 360-400 h·ng/mL 400-440 h·ng/mL 440-480 h·ng/mL. In certain embodiments, the $AUC_{0-\infty}$, is about 80-120 h·ng/mL, 120-160 h·ng/mL, 160-200 h·ng/mL, 200-240 h·ng/mL, 240-280 h·ng/mL, 280-320 h·ng/mL, 320-360 h·ng/mL, 360-400 h·ng/mL 400-440 h·ng/mL 440-480 h·ng/mL. In certain embodiments, the $C_{max}$ is about 8-12 ng/mL, 12-16 ng/mL, 16-20 ng/mL, 20-24 ng/mL, 24-28 ng/mL, 28-32 ng/mL, 32-36 ng/mL, 36-40 ng/mL, 40-44 ng/mL. In certain embodiments, the $T_{max}$, is 4-6 hrs, 6-8 hrs, 8-10 hrs, 10-12 hrs, 12-14 hrs.

In one embodiment, provided herein is a transdermal delivery system which comprises: (i) a backing layer; (ii) a silicone layer; (iii) a drug-containing matrix layer comprising methylphenidate free base, styrene-butadiene block copolymer rubber comprising a hydrogenated synthetic hydrocarbon tackifier; and (iv) a release liner.

Also provided herein is a method of making the transdermal delivery system.

In one embodiment, the method of making the transdermal delivery system comprises the following steps: First, a desired amount of methylphenidate is dissolved into styrene-butadiene copolymer comprising a hydrogenated synthetic hydrocarbon tackifier with solvent to form a drug-containing mixture. Examples of solvents that may be used are toluene, hexane, heptane, ethyl acetate or other solvents appropriate for dissolving methylphenidate or a pharmaceutically acceptable salt thereof. Then, optionally, enhancers and other excipients are added into the mixture. After gentle mixing for 20 minutes or until every component is uniformly dispersed, a matrix is created. Next, the mixture allowed it to stand to deaerate. Vacuum and centrifugation may be employed to shorten the deaeration time. A silicone adhesive layer is laminated onto one side of a supportive backing layer. After deaeration of the mixture, laminate the matrixed mixture uniformly onto silicone adhesive layer of the supportive backing layer with controlled thickness in order to achieve a wet film. Next, dry the wet film in high temperature and/or under strong fan to eliminate the solvent. The dried film will then be laminated with a releasing liner to protect the adhesive side of dry film which is then cropped into desired dimension and formed the patch product.

Further provided herein is a method for controlled and sustained delivery of therapeutic amounts of methylphenidate or its pharmaceutically acceptable salt to a subject.

In some embodiments, the method includes a controlled and sustained drug delivery system useful to deliver Methylphenidate and its salt to a patient. The system comprises delivery of substantially homogeneous particles. In certain embodiments, the substantially homogeneous particles are dispersed in a rubber-based polymer matrix. Also disclosed is the method of preparing a drug-containing matrix.

When compared with other methylphenidate transdermal delivery system, the present transdermal delivery system provides 1.2-3, 3-4, 4-5, 5-6, 6-7, 7-8, 8-9, 9-10, 10-11, or 11-12 folds higher flux rate. In particular, the present methylphenidate transdermal delivery system provides 2-3, 3-4, 4-5, 5-6, 6-7, 7-8, or 8-9 folds higher flux rate as compared with a control methylphenidate transdermal delivery system that does not comprise a silicone adhesive layer.

In certain embodiments, the transdermal delivery system provides effective administration of methylphenidate at a flux rate ranging from about 6 μg/cm²/hr-100 μg/cm²/hr. In certain embodiments, the transdermal delivery system provides effective administration of methylphenidate at a flux rate ranging from about 6 μg/cm²/hr-10 μg/cm²/hr, 10 μg/cm²/hr-15 μg/cm²/hr, 15 μg/cm²/hr-20 μg/cm²/hr, 20 μg/cm²/hr-25 μg/cm²/hr, 25 μg/cm²/hr-30 μg/cm²/hr, 30 μg/cm²/hr-35 μg/cm²/hr, 35 μg/cm²/hr-40 μg/cm²/hr, 40 μg/cm²/hr-45 μg/cm²/hr, 45 μg/cm²/hr-50 μg/cm²/hr, 50 μg/cm²/hr-55 μg/cm²/hr, 55 μg/cm²/hr-60 μg/cm²/hr, 60 μg/cm²/hr-65 μg/cm²/hr, 65 μg/cm²/hr-70 μg/cm²/hr, 70 μg/cm²/hr-75 μg/cm²/hr, 75 μg/cm²/hr-80 μg/cm²/hr, 80 μg/cm²/hr-85 μg/cm²/hr, 85 μg/cm²/hr-90 μg/cm²/hr, 90 μg/cm²/hr-95 μg/cm²/hr, or 95 μg/cm²/hr μg/cm²/hr-100 μg/cm²/hr.

In certain embodiments, the transdermal delivery system provides effective administration of methylphenidate at a flux rate ranging from about 6 μg/cm²/hr-10 μg/cm²/hr, 10 μg/cm²/hr-15 μg/cm²/hr, 15 μg/cm²/hr-20 μg/cm²/hr, 20 μg/cm²/hr-25 μg/cm²/hr, 25 μg/cm²/hr-30 μg/cm²/hr, 30 μg/cm²/hr-35 μg/cm²/hr, 35 μg/cm²/hr-40 μg/cm²/hr, 40 μg/cm²/hr-45 μg/cm²/hr, 45 μg/cm²/hr-50 μg/cm²/hr, 50 μg/cm²/hr-55 μg/cm²/hr, 55 μg/cm²/hr-60 μg/cm²/hr, 60 μg/cm²/hr-65 μg/cm²/hr, 65 μg/cm²/hr-70 μg/cm²/hr, 70 μg/cm²/hr-75 μg/cm²/hr, 75 μg/cm²/hr-80 μg/cm²/hr, 80 μg/cm²/hr-85 μg/cm²/hr, 85 μg/cm²/hr-90 μg/cm²/hr, 90 μg/cm²/hr-95 μg/cm²/hr, or 95 μg/cm²/hr μg/cm²/hr-100 μg/cm²/hr, for at least 2-4 hours, 4-6 hours, 6-8 hours, 8-10 hours, 10-12 hours, 12-14 hours, 14-16 hours, 16-18 hours, 18-20 hours, 20-22 hours, or 22-24 hours after treatment is initiated.

In certain embodiments, the transdermal delivery system provides a therapeutically effective flux rate of methylphenidate ranging from about 6 μg/cm²/hr-10 μg/cm²/hr, 10 μg/cm²/hr-15 μg/cm²/hr, 15 μg/cm²/hr-20 μg/cm²/hr, 20 μg/cm²/hr-25 μg/cm²/hr, 25 μg/cm²/hr-30 μg/cm²/hr, 30 μg/cm²/hr-35 μg/cm²/hr, 35 μg/cm²/hr-40 μg/cm²/hr, 40 μg/cm²/hr-45 μg/cm²/hr, 45 μg/cm²/hr-50 μg/cm²/hr, 50 μg/cm²/hr-55 μg/cm²/hr, 55 μg/cm²/hr-60 μg/cm²/hr, 60 μg/cm²/hr-65 μg/cm²/hr, 65 μg/cm2/hr-70 μg/cm²/hr, 70 μg/cm²/hr-75 μg/cm²/hr, 75 μg/cm²/hr-80 μg/cm²/hr, 80 μg/cm2/hr-85 μg/cm²/hr, 85 μg/cm2/hr-90 μg/cm²/hr, 90 μg/cm²/hr-95 μg/cm2/hr, or 95 μg/cm²/hr g/cm²/hr-100 μg/cm2/hr, for at least 2-4 hours, 4-6 hours, 6-8 hours, 8-10 hours, 10-12 hours, 12-14 hours, 14-16 hours, 16-18 hours, 18-20 hours, 20-22 hours, or 22-24 hours after treatment is initiated.

In certain embodiments, the drug-containing matrix layer contains from about 2% to about 20% w/w methylphenidate and provides a therapeutically effective flux rate ranging from about 6 μg/cm²/hr-10 μg/cm²/hr, 10 μg/cm²/hr-15 μg/cm²/hr, 15 μg/cm²/hr-20 μg/cm²/hr, 20 μg/cm²/hr-25 μg/cm²/hr, 25 μg/cm²/hr-30 μg/cm²/hr, 30 μg/cm²/hr-35 μg/cm²/hr, 35 μg/cm²/hr-40 μg/cm²/hr, 40 μg/cm²/hr-45 μg/cm²/hr, 45 μg/cm²/hr-50 μg/cm²/hr, 50 μg/cm²/hr-55 μg/cm²/hr, 55 μg/cm²/hr-60 μg/cm²/hr, 60 μg/cm²/hr-65 μg/cm²/hr, 65 μg/cm²/hr-70 μg/cm²/hr, 70 μg/cm²/hr-75 μg/cm²/hr, 75 μg/cm²/hr-80 μg/cm²/hr, 80 μg/cm²/hr-85 μg/cm²/hr, 85 μg/cm²/hr-90 μg/cm²/hr, 90 μg/cm²/hr-95 μg/cm²/hr, or 95 μg/cm²/hr g/cm²/hr-100 μg/cm²/hr, for at least 2-4 hours, 4-6 hours, 6-8 hours, 8-10 hours, 10-12 hours, 12-14 hours, 14-16 hours, 16-18 hours, 18-20 hours, 20-22 hours, or 22-24 hours after treatment is initiated.

In certain embodiments, the drug-containing matrix layer releases 40%-50%, 50%-60%, 60%-70% or 70%-80% of methylphenidate within 10-12 hours after treatment is initiated.

In certain embodiments, the drug-containing matrix layer is color-stable and lacks crystal growth of the active ingredient, over an extended storage period of at least 2 years at room temperature.

In one embodiment, the transdermal delivery system comprises: (i) a silicone adhesive layer; and (ii) a drug-containing matrix layer comprising: (a) methylphenidate or its pharmaceutically acceptable salt; and (b) a rubber-based polymer that comprises a hydrogenated synthetic hydrocarbon tackifier, wherein the transdermal delivery system has a flux rate ranging from about 6 µg/cm$^2$/hr-100 µg/cm$^2$/hr between 2-18 hours after treatment is initiated.

Provided herein is a method for delivering drugs to a patient comprising the step of administering the transdermal delivery system disclosed herein.

Provided herein is a method for administering methylphenidate to a human subject in need thereof, which method comprises: (1) providing a transdermal delivery system comprising: (i) a silicon layer; (ii) a drug-containing matrix layer that comprises at least about 2% to about 20% w/w methylphenidate or its pharmaceutically acceptable salt thereof which provides a therapeutically effective flux rate ranging from about 6 µg/cm$^2$/hr-10 µg/cm$^2$/hr, 10 µg/cm$^2$/hr-15 µg/cm$^2$/hr, 15 µg/cm$^2$/hr-20 µg/cm$^2$/hr, 20 µg/cm$^2$/hr-25 µg/cm$^2$/hr, 25 µg/cm$^2$/hr-30 µg/cm$^2$/hr, 30 µg/cm$^2$/hr-35 µg/cm$^2$/hr, 35 µg/cm$^2$/hr-40 µg/cm$^2$/hr, 40 µg/cm$^2$/hr-45 µg/cm$^2$/hr, 45 µg/cm$^2$/hr-50 µg/cm$^2$/hr, 50 µg/cm$^2$/hr-55 µg/cm$^2$/hr, 55 µg/cm$^2$/hr-60 µg/cm$^2$/hr, 60 µg/cm$^2$/hr-65 µg/cm$^2$/hr, 65 µg/cm$^2$/hr-70 µg/cm$^2$/hr, 70 µg/cm$^2$/hr-75 µg/cm$^2$/hr, 75 µg/cm$^2$/hr-80 µg/cm$^2$/hr, 80 µg/cm$^2$/hr-85 µg/cm$^2$/hr, 85 µg/cm$^2$/hr-90 µg/cm$^2$/hr, 90 µg/cm$^2$/hr-95 µg/cm$^2$/hr, or 95 µg/cm$^2$/hr µg/cm$^2$/hr-100 µg/cm$^2$/hr, for at least 2-4 hours, 4-6 hours, 6-8 hours, 8-10 hours, 10-12 hours, 12-14 hours, 14-16 hours, 16-18 hours, 18-20 hours, 20-22 hours, or 22-24 hours after treatment is initiated; and (2) applying the transdermal delivery system to an area of skin of the subject in an amount sufficient to provide a therapeutic concentration of methylphenidate in the bloodstream of the subject.

In certain embodiments, the method comprises applying up to about 4 mg-60 mg of methylphenidate to a skin surface area of about 2 cm$^2$-60 cm$^2$.

In certain embodiments, the method comprises applying the transdermal delivery system on the abdomen, thigh, behind an ear, or on a shoulder or upper arm of a subject.

In certain embodiment, the method comprises applying the transdermal delivery system in a daily single dose.

In certain embodiments, the transdermal therapeutic system applied in the method provides a rate of administration of methylphenidate ranging from about 6-100 g per hour over 16 hours after treatment is initiated.

In certain embodiments, the transdermal therapeutic system provides sustained, steady-state delivery of about 6-100 µg per hour over 10 hours after treatment is initiated.

In certain embodiments, the transdermal therapeutic system provides sustained, steady-state delivery of about 6-100 µg per hour over 16 hours after treatment is initiated.

In certain embodiments, the transdermal therapeutic system provides sustained, steady-state delivery of about 6-100 µg per hour over 18 hours after treatment is initiated.

In certain embodiments, the transdermal therapeutic system provides sustained, steady-state delivery of about 6-100 µg per hour over 24 hours after treatment is initiated.

Also described herein is a transdermal delivery system used to treat or prevent diseases in a subject. In a specific embodiment, the subject is a mammal. In a specific embodiment, the subject is human. In one embodiment, provided herein is a method of treating a disease comprising administering to a subject, a transdermal delivery system comprising a therapeutically effective amount of methylphenidate or its salt.

Also disclosed is a kit comprising the transdermal delivery system provided herein. The kit comprises a carrier being compartmentalized to receive in close confinement one or more containers comprising one of the separate elements to be used in the method. The kit also contains instructions for administering the transdermal delivery system.

A kit as provided herein comprises a unit dose of methylphenidate or its salt provided herein, such that when administered to a subject, a therapeutically or prophylactically effective plasma level of the compound or composition can be maintained in the subject for at least 1-2, 2-4, 4-6, 6-8, 8-10, 10-12, 12-14, 14-16, 16-18, 18-20, 20-22, 22-24 hours. In certain embodiments, the therapeutically or prophylactically effective plasma level of the compound or composition can be maintained in the subject for at least 1, 2, 3, 4, 5, and 7 day.

These and other aspects, features, and advantages can be appreciated from the accompanying description of certain embodiments of the disclosure and the accompanying drawing figures and claims.

4.1 BRIEF DESCRIPTION OF FIGURES

FIG. 1 shows is a schematic diagram comparing permeation mechanism of active ingredient from a transdermal delivery system that does not comprise a silicone layer versus a transdermal delivery system that comprises a silicon layer.

FIG. 2 shows the average permeation rate comparison between two transdermal delivery system. Bottom curve: Transdermal delivery system comprising 17% Methylphenidate without a silicon layer. Top curve: Transdermal delivery system comprising a silicon adhesive layer and a drug-containing layer comprising 17% Methylphenidate. The graph measures flux rate (g/ml/cm$^2$/hr) vs. time (Hr).

FIG. 3 shows the average cumulative amount comparison between two transdermal delivery system. Bottom curve: Transdermal delivery system comprising 17% Methylphenidate without a silicon adhesive layer. Top curve: Transdermal delivery system comprising a silicon adhesive layer and a drug-containing layer comprising 17% Methylphenidate. The graph measures cumulative amount permeated (µg/cm$^2$) vs. time (Hr).

4.2 DEFINITIONS

Figure 1:
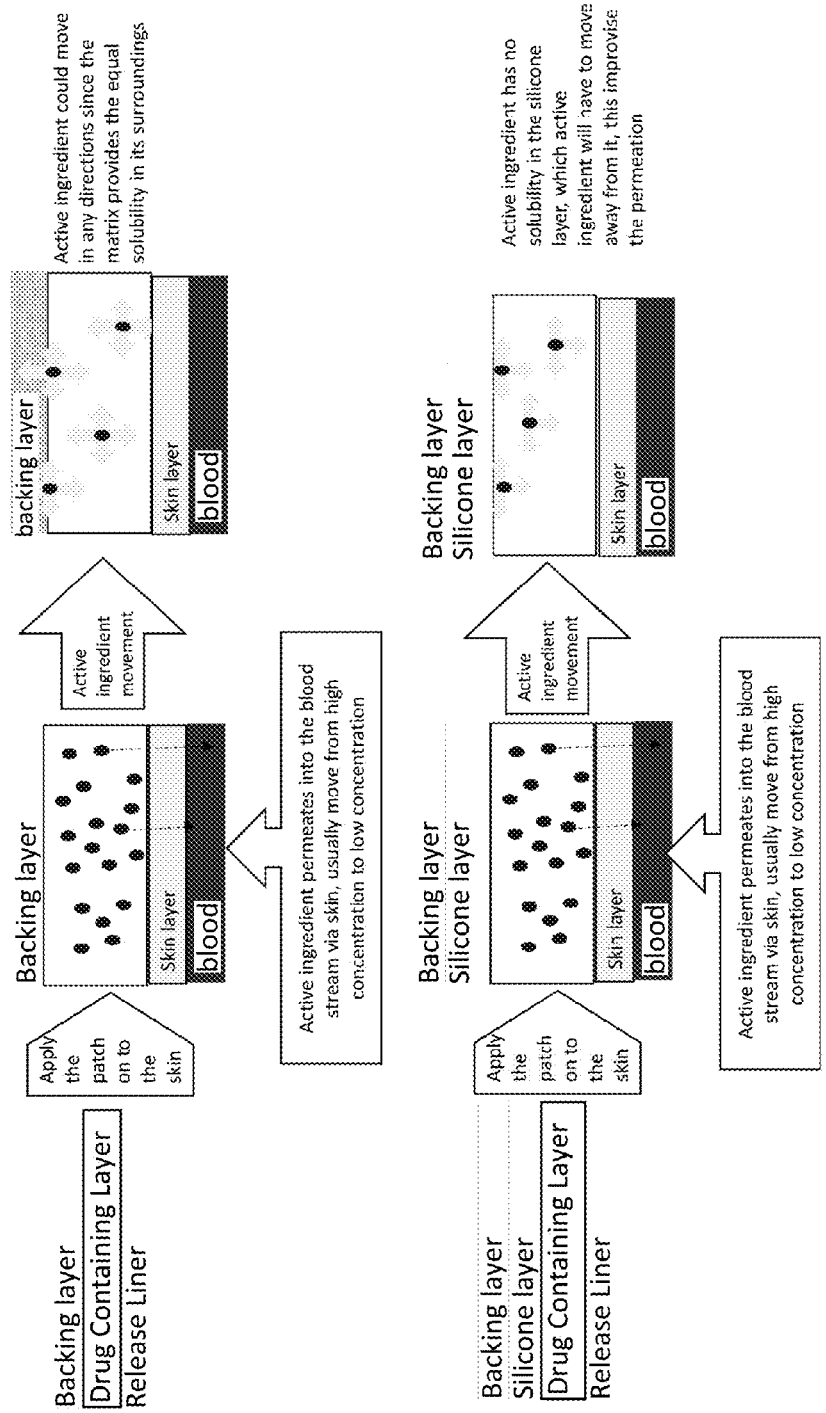

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgus monkey, a chimpanzee and a human). In one embodiment, the subject is a human.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "preventing" and "prevention" of any disease and disorder refers to the prevention of a disorder or one or more symptoms thereof. Preventing and prevention is to impede the onset, development, and progression of disorder or symptoms.

As used herein, the term "about" is defined as a deviation of +5% from a numerical value.

The term "Methylphenidate or its pharmaceutically acceptable salt" means methylphenidate free base or a methylphenidate salt that induces a desired pharmacological or physiological effect, and includes agents that are therapeutically effective or prophylactically effective. The terms also encompass pharmacologically active derivatives and analogs of those active agents specifically mentioned herein, including, but not limited to, salts, esters, amides, sulfates, prodrugs, active metabolites, inclusion complexes and the like.

The term "effective amount" or "a therapeutically effective amount" of a drug or pharmacologically active agent is intended to mean a nontoxic but sufficient amount of the drug or active agent for providing the desired therapeutic effect. The amount that is "effective" will vary from subject to subject, depending on the age and general condition of the individual, the particular active agent or agents, and the like. An appropriate "effective" amount in any individual case may be determined by one of ordinary skill in the art using routine experimentation.

As used herein, the term "styrene-butadiene block copolymer" is defined as copolymer of monomers containing styrene and butadiene.

As used herein, the terms "topical" and topically" mean application to a skin or mucosal surface of a mammal, while the terms "transdermal" means passage through the skin or mucosa (including oral, buccal, nasal, rectal and vaginal mucosa), into systemic circulation. Thus, the compositions described herein may be applied topically to a subject to achieve transdermal delivery of methylphenidate.

As used herein, the term "drug-containing matrix" means a composition comprising one or more drugs, such as methylphenidate, and a rubber-based polymer optionally comprising a hydrogenated synthetic hydrocarbon tackifier.

5. DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter. It is to be understood that particular features, structures, or characteristics described may be combined in various ways in one or more implementations.

5.1 Multi-Layer Structure of the Transdermal Delivery System

Disclosed herein is a flexible, finite system that is a solid form capable of conforming to the surface with which it comes into contact. The system is capable of maintaining the contact in such solid form so as to facilitate topical application without adverse physiological response, and without being decomposed by contact on dry or wet surfaces during administration to a subject. Flexible, finite systems that are known in the art include, films, plasters, dressings, and bandages, as well as multi-layer delivery systems in which the drug is solubilized or contained in a reservoir or depot separate from the matrix which attaches directly to the skin or mucosa. In one embodiment, the drug is in a matrix.

In one embodiment, the transdermal delivery system described herein comprises a backing layer, a silicone adhesive layer, a drug-containing matrix layer comprising: (i) methylphenidate and its pharmaceutically acceptable salt; (ii) rubber-based polymer that comprises a hydrogenated synthetic hydrocarbon tackifier, and a release liner. In one embodiment, the rubber-based polymer is styrene-butadiene block copolymer. In one embodiment, the rubber-based polymer is not styrene-isoprene-styrene polymer. In one embodiment, the rubber-based polymer is not polyisobutylene.

Methylphenidate (a-phenyl-2-piperidineacetic acid methyl ester) is a chiral drug. While commercially available methylphenidate products (such as the oral product Ritalin® tablets and the transdermal product Daytrana®) patch include a 50:50 (racemic) mixture of d- and l-threo-methylphenidate, it is believed that the d-threo-methylphenidate isomer has greater pharmacological activity. The compositions described herein may be formulated with any isomer of methylphenidate, although compositions comprising a racemic mixture of d- and l-threo-methylphenidate, or comprising primarily the d-threo-methylphenidate isomer may be most commercially relevant.

The compositions described herein may be formulated with methylphenidate free base ("methylphenidate base"), any pharmaceutically acceptable salt thereof, or mixtures thereof. Exemplary suitable pharmaceutically acceptable salts of methylphenidate are salts of weak inorganic and organic acids, and quaternary ammonium salts. These include without limitation, salts with acids such as sulfuric, phosphoric, hydrochloric, hydrobromic, hydriodic, sulfamic, citric, lactic, maleic, malic, succinic, tartaric, cinnamic, acetic, benzoic, gluconic, or ascorbic acid, or quaternary ammonium salts with organic esters of sulfuric, hydrohalic, or aromatic sulfonic acids, such as methyl chloride, methyl bromide, ethyl chloride, propyl chloride, butyl chloride, isobutyl chloride, benzylchloride, benzyl bromide, phenethyl bromide, naphthylmethyl chloride, dimethyl sulfate, methyl benzenesulfonate, ethyl toluenesulfonate, ethylene chlorohydrin, propylene chlorobydrin, allyl bromide, methylallyl bromide or crotyl bromide esters.

Methylphenidate, including methylphenidate base in particular, has a secondary amine moiety and a methyl ester moiety, and is unstable and undergoes degradation in the presence of reactive functional groups, such as active hydrogen atoms or functional groups with hydrogen atoms available for chemical reaction or interaction with methylphenidate, such as, for example, carboxyl, hydroxyl, amine, thiol, silanol or epoxy groups, which may be present in polymers, enhancers, excipients and other components that typically may be used in transdermal compositions. Major degradants of methylphenidate include ritalinic acid and erythol isomer, whose concentrations increase significantly with increasing amounts (by weight) of functional groups. Such degradation can greatly reduce the amount of the active species present in a composition after storage, thus reducing the amount of active methylphenidate available for drug delivery. Thus, in some embodiments, the compositions described herein are formulated without components that have such functional groups. That is, in some embodiments, the compositions described herein are formulated only with non-reactive components as defined above and discussed in more detail below.

The compositions described herein include a therapeutically effective amount of methylphenidate or pharmaceutically acceptable salt thereof. Generally, the amount of methylphenidate is from about 5% to about 20%, including from about 5% to about 15%, such as from about 10% to about 19% by weight, or from about 15% to about 18% by weight, based on the total dry weight of the drug-containing matrix. In specific embodiments, the drug-containing matrix comprises about 17% by weight methylphenidate, based on the total dry weight of the drug-containing matrix.

In accordance with any of the embodiments described herein, the composition may include from about 20 to about 225 mg per unit of methylphenidate base or an equivalent amount of a pharmaceutically acceptable salt thereof.

The amount of methylphenidate and its pharmaceutically acceptable salt present in the drug-containing matrix layer may vary. In certain embodiments, the amount of methylphenidate and its pharmaceutically acceptable salt deliver methylphenidate ranges from about 4 mg to about 60 mg. In certain embodiments, the methylphenidate and its pharmaceutically acceptable salt ranges from about 4-8 mg, about 8-10 mg, about 10-12 mg, about 12-14 mg, about 14-16 mg, about 16-18 mg, about 18-20 mg, about 20-24 mg, about 24-28 mg, about 28-30 mg, about 30-35 mg, about 35-40 mg, about 40-45 mg, about 45-50 mg, about 50-55 mg, or about 55-60 mg per unit of the transdermal delivery system. In one embodiment, a unit of the transdermal delivery system is one dose of the transdermal delivery system. In one embodiment, one dose is one patch. In certain embodiments, the methylphenidate and its pharmaceutically acceptable salt present in the drug-containing matrix layer is about 0.01-0.05%, about 0.05%-0.1%, about 0.1-0.2%, about 0.2-0.5%, about 0.5-1%, about 1-2%, about 2-4%, about 2-5%, about 5-6%, about 6-7%, about 7-8%, about 8-9%, about 9-10%, about 10-13%, about 13-14%, about 14-15%, about 15-16%, about 16-17%, about 17-18%, about 18-19%, about 19-20%, or about 20-25%, by weight based on the total weight of the drug-containing matrix layer. In certain embodiments, the methylphenidate and its pharmaceutically acceptable salt is about 0.01-5% by weight based on the total weight of the drug-containing matrix layer. In certain embodiments, the methylphenidate and its pharmaceutically acceptable salt is about 1-16% by weight based on the total weight of the drug-containing matrix layer. In certain embodiments, the methylphenidate and its pharmaceutically acceptable salt is about 0.5-1, 1-2.5, 2.5-3, 3-4, 4-5, 5-6, 6-7, 7-8, 8-9, 9-10, 10-11, 11-12, 12-13, 13-14, 14-15, 15-16, 16-17, 17-18, 18-19, 19-20% by weight based on the total weight of the drug-containing matrix layer.

The drug-containing matrix layer comprises methylphenidate or its pharmaceutically acceptable salt. In one embodiment, the methylphenidate is methylphenidate free base. In certain embodiments, the drug-containing matrix layer includes one or more active agents, which agents are methylphenidate and its pharmaceutically acceptable salt.

5.1.1 Silicone Adhesive Layer

It is discovered that a silicone adhesive layer in the methylphenidate transdermal delivery system of the present disclosure significantly increases the flux and efficiency of the patch. The presently disclosed methylphenidate transdermal delivery system has increased drug loading capacity and drug release sustainability and achieved a desired skin penetration rate and adhesion property.

In certain embodiment, the silicone adhesive layer comprises 10-50%, 50-80%, 80-90%, 90-100% of silicone adhesive. In one embodiment, the silicone adhesive layer comprises 100% silicone adhesive. In certain embodiment, the silicone adhesive layer has a thickness of about 1-5 μm, 5-10 μm, 10-20 μm, 20-30 μm, 30-40 μm, 40-50 μm or 50-60 μm.

In one embodiment, the silicon adhesive layer is a uniform layer that has even thickness throughout the layer. There is minimal intermixing of the silicone adhesive layer with the drug-containing matrix layer. In certain embodiments, the silicone adhesive layer act as the backing/impermeable layer. Hartwig R., Kanios D., Bonne S.; Acrylic Polymer Backing Films for Controlling In-Vitro Permeation and Delivery Profile of Estradiol from Transdermal Drug Delivery Systems; AAPS 2004 showed that adding acrylic polymer backing film could reduce the permeation rate and delivery profile. The addition of a silicon adhesive layer actually increases the permeation rate and delivery profile.

In certain embodiments, the silicone adhesive layer further comprises additional adhesives. Suitable adhesives include (pressure sensitive adhesives made from silicone polymer and resin. The polymer to resin ratio can be varied to achieve different levels of tack, which is useful where the matrix layer is the skin contact layer of a device of the present disclosure. Specific examples of useful silicone adhesives for this purpose which are commercially available include the standard Dow Corning® BIO-PSA series (7-4400, 7-4500 and 7-4600 series) and the amine compatible (endcapped) Dow Corning® BIO-PSA series (7-4100, 7-4200 and 7-4300 series) manufactured by Dow Corning. In certain embodiments, adhesives include Dow Corning® BIO-PSA 7-4201, 7-4202, 7-4301, 7-4302, 7-4501, 7-4502 and 7-4602, with BIO-PSA 7-4201, BIO-PSA 7-4301, BIO-PSA 7-4302 or mixtures thereof, e.g., BIO-PSA 7-4201, BIO-PSA 7-4301 and/or BIO-PSA 7-4302.)

In certain embodiments, the silicone adhesive layer provides at least 60-70% increase in flux as compared to a control transdermal system that does not comprise the silicone adhesive layer. In certain embodiments, the silicone adhesive layer provides at least 60-70% increase in average cumulative amount of drug delivery as compared to a control transdermal system that does not comprise the silicone adhesive layer.

5.1.2. Drug-Containing Matrix Layer

In certain embodiments, the drug-containing matrix layer comprises rubber-based polymer. In certain embodiments, the rubber-based polymers include, but are not limited to, styrenic block polymers and combinations thereof. Suitable styrenic block copolymer-based adhesives include, but are not limited to, styrene-butadiene-styrene copolymer (SBS).

In certain embodiments, the drug-containing matrix layer comprises a rubber-based polymer that comprises a hydrogenated synthetic hydrocarbon tackifier. In certain embodiments, the hydrogenated synthetic hydrocarbon tackifier is rosin esters, terpene and or hydrocarbon. In one embodiment, the polymer matrix includes one or more C5 to C9 hydrogenated hydrocarbon resins. In one embodiment, the polymer matrix does not include one or more C5 to C9 hydrogenated hydrocarbon resins. In one embodiment, the hydrogenated synthetic hydrocarbon is fully saturated. In certain embodiments, the hydrogenated hydrocarbon is partially saturated. In certain embodiments, the hydrogenated hydrocarbon comprises at least 1, 2, 3, 4 carbon atoms that are not fully hydrogenated.

In certain embodiments, the drug-containing matrix layer comprises a rubber-based polymer including natural or synthetic polyisoprene, polybutylene, polyisobutylene, styrene-butadiene polymers, styrene-isoprene-styrene block copolymers, hydrocarbon polymers, such as butyl rubber, halogen-containing polymers, such as polyacrylic-nitrile, polytetrafluoroethylene, polyvinylchloride, polyvinylidene chloride, and polychlorodiene, and other copolymers thereof. In some embodiments, the polymer matrix comprises one or more polyisobutylene polymers. In some embodiments, the polymer matrix comprises one or more styrene-isoprene-styrene block copolymers. In some embodiments, the polymer matrix comprises one or more one or more polyisobutylene polymers and one or more styrene-isoprene-styrene block copolymers.

In certain embodiments, the drug-containing matrix layer may exclude any of the previously listed natural or synthetic polymers or copolymers as disclosed above.

The drug-containing matrix layer may include a pressure sensitive adhesive. The terms "pressure sensitive adhesive" means an adhesive that forms an adhesive bond when pressure is applied to adhere the adhesive with a surface. In certain embodiments, the degree of bond strength is proportional to the amount of pressure that is used to apply the adhesive to the surface.

In certain embodiments, the drug-containing matrix layer does not contain acrylic polymers.

In certain embodiments, the drug-containing matrix layer comprises a tackifier. In certain embodiments, the drug-containing matrix layer does not comprise a tackifier.

In certain embodiments, the drug-containing matrix layer comprises a tackifier that is not present in the rubber-based polymer. In certain embodiment, the drug-containing matrix layer does not comprise a tackifier except a hydrogenated synthetic hydrocarbon tackifier.

In certain embodiments, the tackifier present in the drug-containing matrix layer is about 3-10%, about 10-30%, about 30-50%, about 50-60%, about 60-65%, about 65-70%, about 70-75%, about 75-80%, about 75-80%, about 80-90%, about 90-95%, about 95-96%, about 96-97%, about 97-98%, about 98-99%, by weight based on the total weight of the drug-containing matrix layer. In certain embodiments, the tackifier is about 30-85% by weight based on the total weight of the drug-containing matrix layer. In certain embodiments, the tackifier is about 30-60% by weight based on the total weight of the drug-containing matrix layer.

In certain embodiments, the drug-containing matrix layer comprises an enhancer composition that enhances drug permeation. The enhancer composition facilitates the absorption of the active agent through the skin of the subject.

In certain embodiments, the antioxidant may be present in an amount ranging from about 0.001 to 5.0%, about 0.05%, about 0.001-0.005%, about 0.005-0.01%, about 0.01-0.05%, about 0.05-0.1%, about 0.1-0.5%, about 0.5-1%, about 1-3%, about 3-5% by weight based on the total weight of the drug-containing matrix layer.

In certain embodiments, the drug-containing matrix layer may contain fillers which include, but are not limited to: metal oxides (such as zinc oxide and titanium oxide), metal salts (such as calcium carbonate, magnesium carbonate and zinc stearate), silicic acid compounds (such as kaolin, talc, bentonite, Aerosil, hydrous silica, aluminum silicate, magnesium silicate and magnesium aluminometasilicate) and metal hydroxides (such as aluminum hydroxide). Where present, such fillers may be 1 to 75%, such as 2 to 50% by weight based on the total weight of the drug-containing matrix layer.

In certain embodiments, the drug-containing matrix layer includes a solvent which includes but is not limited to a volatile solvent or a non-volatile solvent (i.e., a solvent that is non-volatile as compared to acetone, isopropanol or water, but may nonetheless exhibit some volatility), such as dimethyl sulfoxide (DMSO), N-methylpyrrolidone, dimethyl isosorbide, propylene glycol, hexylene glycol and benzyl alcohol. In one embodiment, the solvent is diethylene glycol monoethyl ether. In certain embodiments, the solvent is Transcutol® P. The drug-containing matrix layer comprises a solvent in an amount of about 0.1-1%, about 1-5%, about 5-10%, about 10-15%, about 15-20%, about 20-30% by weight based on the total weight of the drug-containing matrix layer. In certain embodiments, the drug-containing matrix layer comprises one or more solubilizers and/or enhancers. In certain embodiments, the solubilizers and/or enhancers are ethyl acetate, isopropyl alcohol, methanol, tetrahydrofuran, oleic Acid, SPAN 80, isopropyl myristate, Brij 30, Tween 80, squalane, dipropylene glycol, limonens, N-lauroyl sarcosine, octanol, polyoxyethylene lauryl ether, Crodasinic LS 30, glycerine, Crodamol, glyceryl monooleate, oleyl alcohol, glyceryl dibehenated, octyldodecanol, isopropyl palmitate, Di-tert-butyl-4-Methyl-Phenol, ethyloleate, dodecanol, myristyl alcohol, oleyl oleate, N-Heptane, N-Hexane, isobutyl alcohol, polysorbate 80, chloroform.

The drug-containing matrix layer of the transdermal delivery system may vary in thickness. In certain embodiments, the drug-containing matrix layer has a thickness within a range that is sufficient to provide for the desired extended delivery of a therapeutically effective amount of the active agent to the subject. In certain embodiments, the thickness of the formulation is chosen in view of the desired transdermal delivery rate of the active agent and the target dosage. In certain embodiments, the thickness of the drug-containing matrix layer is about 10 µm to about 15 µm, about 15 µm to about 20 µm, about 20 µm to about 25 µm, about 25 µm to about 30 µm, about 30 µm to about 35 µm, about 35 µm to about 40 µm, about 40 µm to about 45 µm, about 45 µm to about 50 µm, about 50 µm to about 55 µm or about 55 µm to about 150 µm.

5.1.3 Backing Layer

In certain embodiments, the transdermal delivery system includes a backing layer (e.g., support layer). The backing may be flexible to an extent that it can be brought into close contact with a desired topical location of a subject. The backing may be fabricated from a material that does not absorb the active agent, and does not allow the active agent to be released from the backing side of the transdermal formulation. Backing materials of interest may be occlusive (i.e., impermeable), semi-occlusive or breathable (permeable). The backing may include, but is not limited to, non-woven fabrics, woven fabrics, films (including sheets), foils, porous bodies, foamed bodies, paper, composite materials obtained by laminating a film on a non-woven fabric or fabric, and combinations thereof. Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly (ester ether), polyurethane, polyacrylic resins, polyvinyl alcohol, styrene-isoprene-styrene copolymers, and styrene-ethylene-propylene-styrene copolymers; and combinations thereof.

Fabrics may include, but are not limited to: cotton, rayon, polyacrylic resins, polyester resins, polyvinyl alcohol, and combinations thereof. Films may include, but are not limited to the following: polyolefin resins such as polyethylene (including low density and high density polyethylene (LDPE, HDPE) and polypropylene; polyacrylic resins such as polymethyl methacrylate and polyethyl methacrylate; polyester resins such as polyethylene terephthalate, polychloro-tri-fluoro-ethylene, acrylonitrile methyl acrylate copolymer, polybutylene terephthalate and polyethylene naphthalate; and polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Foils may include metallic foils, e.g., aluminum foils, etc. Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric. In certain embodiments, the backing includes a polyester, such as polyethylene terephthalate (PET).

In certain embodiments, the backing layer is in contact with a surface of the drug-containing matrix layer. For example, where the transdermal delivery system is configured so that one surface of the drug-containing matrix layer contacts the skin upon application, the backing will be in contact with an opposing surface of the drug-containing matrix layer.

In certain embodiments, suitable backing layer includes ethylene vinyl acetate films laminated to a polyester, ethylene vinyl acetate films laminated to a metallized polyester, polyethylene or polyolefin backings. The backing layer should be thick enough to resist wrinkling which may arise upon prolonged periods in storage and through the movement of a subject's skin. Typically, the backing layer is from about 50 microns to about 100 microns in thickness. In certain embodiments, the backing layer has a larger surface than the drug-containing matrix layer. In certain embodiments, the backing layer ranges from about 0.01 mm to at least 10 mm larger than the drug-containing matrix layer.

5.1.4 Release Liner

In certain embodiments, the transdermal delivery system comprises a release liner. In certain embodiments, a release liner is provided on the drug-containing matrix layer, and specifically on a surface of the drug-containing matrix layer that is distal (i.e., opposite) from the backing layer. The release liner may facilitate the protection of the drug-containing matrix layer before use of the transdermal delivery system. In certain embodiments, the release liner is configured to be removable from the drug-containing matrix layer without retaining the drug-containing matrix layer.

The release liner may be any convenient material. In certain embodiments, the release liner includes polyesters, such as polyethylene terephthalate, polypropylene and combinations thereof. In certain embodiments, the release liner includes a coated substrate, which, for example, may be prepared by treating one side of polyethylene-coated wood free paper, polyolefin-coated glassine paper, a polyethylene terephthalate (polyester) film, a polypropylene film, with a silicone treatment. In certain instances, the release layer includes a polyester film with a silicone treatment.

5.2 Dosage and Delivery of Active Agents

According to the present disclosure, the inventors have found that methylphenidate may be administered to the human body via topical application delivery for the purpose of treating Attention Deficit Disorder (ADD) and Attention Deficit/Hyperactivity Disorder (ADHD) if the transdermal delivery system comprises a silicone adhesive layer and drug-containing matrix layer. In certain embodiments, the methylphenidate is delivered in an amount effective to achieve substantially zero-order kinetics 2 hours after application of the transdermal delivery system. The present composition would provide a steady release of methylphenidate to the patient via topical application route. In certain embodiments, the transdermal delivery system has a delivery rate of about 0.5 mg/24 hours to about 100 mg/24 hours of methylphenidate. In certain embodiments, the transdermal delivery system has a delivery rate of about 2.5 mg/24 hours to about 60 mg/24 hours to achieve a therapeutically effective dose in a patient. The administration of methylphenidate orally is 20-60 mg per day. In certain embodiments, the topical application system contains about 20-180 mg of methylphenidate or an effective amount which will not crystallize in the system. In certain embodiments, the amount of methylphenidate in the topical application system is effective to deliver at least 60 mg of the drug to the patient. In certain embodiments, the size of the delivery patch is about 2 $cm^2$ to about 60 $cm^2$. In certain embodiments, the transdermal delivery system delivers about 5 mg per 24 hours and contains about 26.4 mg of methylphenidate base per 10 $cm^2$.

In one embodiment, the transdermal delivery system disclosed herein comprises methylphenidate or its pharmaceutically acceptable salt in an amount to provide a flux of at least 8 ug/$cm^2$ hr to achieve therapeutic blood levels of methylphenidate for at least 2-4, 4-8, 8-10, 10-12, 12-14, 14-16, 16-18, 18-20, 20-22, or 22-24 hours.

In one embodiment, the transdermal delivery system disclosed herein comprises methylphenidate or its pharmaceutically acceptable salt in an amount to provide a dose of at least 5 mg to a patient over 8 hours with a flux of at least 8 ug/$cm^2$ hr for at least 2 hours.

In one embodiment, the transdermal delivery system disclosed herein comprises methylphenidate or its pharmaceutically acceptable salt in an amount sufficient to achieve blood levels of methylphenidate in the range of 1 ng/ml to 25 ng/ml for at least 16 hours.

In one embodiment, the transdermal delivery system disclosed herein comprising methylphenidate or its pharmaceutically acceptable salt in a rubber-based adhesive carrier comprising a hydrogenated synthetic hydrocarbon tackifier, wherein the methylphenidate is present in an amount sufficient to achieve substantially zero order kinetics for delivery to the skin or mucosa of a patient in need thereof over a period of time at least 2 hours, wherein the methylphenidate is present at a therapeutically effective amount that is substantially free of crystals.

The amount of a composition that will be effective in the treatment or prophylactic treatment of Attention Deficit Disorder (ADD) and/or Attention Deficit/Hyperactivity Disorder (ADHD) can be determined by standard clinical techniques. In addition, in vitro or in vivo assays may optionally be employed to help identify optimal dosage ranges. The precise dose to be employed will also depend on the seriousness of the disease or disorder, and should be decided according to the judgment of the practitioner and each patient's circumstances.

Suitable doses of the drug for transdermal delivery are in the range of 0.5 mg/24 hours to 100 mg/24 hours depending on the area to which the compound is administered. Effective doses may be extrapolated from dose-response curves derived from in vitro or animal model test systems. Such animal models and systems are well known in the art.

In certain embodiment, the transdermal delivery system is applied to a subject shortly before the subject goes to sleep. In one embodiment, the transdermal delivery system is applied to a subject 8-10 hours prior to waking up in the morning. In one embodiment, the transdermal delivery system is applied to a subject shortly after awaken from sleep in the morning. In one embodiment, the transdermal delivery system is removed prior to going to sleep in the evening. In certain embodiments, the transdermal delivery system is applied within 2 hours prior to engaging at work or school or other activities while awake. In certain embodiments, the transdermal delivery system is applied to a subject for 2-4, 4-6, 6-8, 8-10, 10-12, 12-14, 14-16, 16-18, 18-20, 20-22, 22-24 hours.

As used herein, the term, "flux" is defined as the absorption of the drug through the skin or mucosa, and is described by Fick's first law of diffusion:

$$J = -D(dCm/dx),$$

where J is the flux in g/cm2/sec, D is the diffusion coefficient of the drug through the skin or mucosa in cm2/sec and Dcm/dx is the concentration gradient of the drug across the skin or mucosa.

The inventors have found that there is a relatively wide range of permeability of normal human skin to methylphenidate and this permeability not only varies from individual to individual and site to site, but is also dependent upon the chemical form of the drug. In certain embodiments, the methylphenidate in the transdermal delivery system is in the base form or a base/basic salt combination, or an ester.

In certain embodiments, a therapeutically effective dose of methylphenidate achieves a therapeutic effect, and is typically in the range of about 0.05 mg/kg to about 1.0 mg/kg/day for both children and adults, and more preferably of about 0.075 mg/kg/day to about 0.3 mg/kg/day.

The presently disclosed transdermal delivery system attains substantially zero-order delivery 6 hours after application to a subject. The transdermal delivery system sustains a substantially zero-order delivery of methylphenidate or its pharmaceutical salts thereof for at least 18 hours, 20 hours or 24 hours. This is ensured by providing enough methylphenidate in the topical composition so as to deliver 15 to 40% of the drug in the first 18 hours.

In one embodiment, the disclosed transdermal delivery system attains at least 18 hours of substantially zero-order delivery. The silicone adhesive layer allows sufficient amounts of methylphenidate to be loaded into the composition, while preserving the methylphenidate in the active form needed for at least 18 hours of substantially zero-order delivery.

The presently disclosed system and methods of delivery of methylphenidate in therapeutic amounts for continuous periods in topical application systems which rely primarily on skin or mucosa permeability to control drug input rate. It is also contemplated that delivery of the drug can be from a rate controlled system in which the system itself controls the maximum rate at which the drug is delivered through the skin or mucosa.

The phrase, "substantially zero-order" as used herein means delivery of methylphenidate through the skin or mucosa at a rate which is approximately constant once steady state is attained. Typical variability contemplated within the scope of this meaning is about a 30% to about 40% difference from the mean in the blood levels of methylphenidate at steady state (3-10 hours after administration).

While the actual flux may vary, in certain embodiments, (e.g., as determined using the skin permeation assay in the Section 6 Examples below) skin permeation rates are about 3-4 µg/cm$^2$/hr, about 4-5 µg/cm$^2$/hr, about 5-6 µg/cm$^2$/hr, about 6-7 µg/cm$^2$/hr, about 7-8 g/cm$^2$/hr, about 8-9 µg/cm$^2$/hr, about 9-10 µg/cm$^2$/hr, about 10-11 µg/cm$^2$/hr, or about 11-12 g/cm$^2$/hr, about 12-15 µg/cm$^2$/hr, about 15-20 µg/cm$^2$/hr, about 20-25 µg/cm$^2$/hr, about 25-30 g/cm$^2$/hr, about 30-35 µg/cm$^2$/hr, about 35-40 µg/cm$^2$/hr, about 40-45 µg/cm$^2$/hr, or about 45-50 g/cm$^2$/hr.

In certain embodiments, the flux is about 13-44 µg/cm$^2$ hr.

In certain embodiments, the transdermal delivery systems are formulated to provide a cumulative delivered amount (also referred to herein as cumulative flux) of the active agent to a subject when the formulation is applied to the skin of a subject for an extended period of time as described infra. In certain embodiments, the transdermal formulations are configured to provide a cumulative delivered amount of the active agent of about 1-100 µg/cm$^2$, about 100-150 µg/cm$^2$, about 150-200 µg/cm$^2$, about 200-250 µg/cm$^2$, about 250-300 µg/cm$^2$, about 300-350 µg/cm$^2$, about 350-400 µg/cm$^2$, about 400-450 µg/cm$^2$, about 450-500 µg/cm$^2$, about 500-550 µg/cm$^2$, about 550-600 µg/cm$^2$, about 600-650 µg/cm$^2$, 650-700 µg/cm$^2$, about 700-750 µg/cm$^2$, 750 m-800 µg/cm$^2$, 800-850 µg/cm2, about 850-900 µg/cm$^2$, about 900-950 µg/cm$^2$, or about 950-1000 µg/cm$^2$.

The size (i.e., area) of the transdermal delivery system may vary, but is within a range of the active agent to the subject. It is also important that the subject wearing the transdermal delivery system finds the system to be easy to apply and comfortable to use for a period of time so as to improve compliance. In certain embodiments, the size of the formulation is chosen in view of the desired transdermal flux rate of the active agent and the target dosage. In certain embodiments, the transdermal delivery system has a size that is about 2-6 cm$^2$, about 6-10 cm$^2$, about 10-20 cm$^2$, about 20-30 cm$^2$, about 30-40 cm$^2$, about 40-50 cm$^2$, about 50-100 cm$^2$, about 100-130 cm$^2$, about 130-140 cm$^2$, about 140-150 cm$^2$ or about 150-200 cm$^2$.

The transdermal delivery system of the present disclosure is formulated to provide a therapeutically effective amount of the active agent to a subject when the topical patch is applied to a skin site of a subject for an extended period of time (e.g., a multi-day period of time). For example, the extended period of time may be a period of time that is about 6-12 hours, about 12-24 hours, about 1-2 days.

In certain embodiments, various formulations, human pharmacokinetics profile and skin permeation properties are shown in Tables 1, 2 and 3. In certain embodiments, the $AUC_{0-t}$ is about 80-120 h·ng/mL, 120-160 h·ng/mL, 160-200 h·ng/mL, 200-240 h·ng/mL, 240-280 h·ng/mL, 280-320 h·ng/mL, 320-360 h·ng/mL, 360-400 h·ng/mL 400-440 h·ng/mL 440-480 h·ng/mL. In certain embodiments, the $AUC_{0-\infty}$ is about 80-120 h·ng/mL, 120-160 h·ng/mL, 160-200 h·ng/mL, 200-240 h·ng/mL, 240-280 h·ng/mL, 280-320 h·ng/mL, 320-360 h·ng/mL, 360-400 h·ng/mL 400-440 h·ng/mL 440-480 h·ng/mL. In certain embodiments, the $C_{max}$ is about 8-12 ng/mL, 12-16 ng/mL, 16-20 ng/mL, 20-24 ng/mL, 24-28 ng/mL, 28-32 ng/mL, 32-36 ng/mL, 36-40 ng/mL, 40-44 ng/mL. In certain embodiments, the $T_{max}$, is 4-6 hrs, 6-8 hrs, 8-10 hrs, 10-12 hrs, 12-14 hrs.

An aspect of the transdermal delivery system of the present disclosure is that it may be stored for extended periods of time without significant degradation and/or significant reduction in activity of the active agent. In certain embodiments, the drug-containing matrix layer comprising methylphenidate or its pharmaceutically acceptable salt is stable for at least 1 year, 2 years, 3 years, 4 years, 5 years, or 6 years. In certain embodiments, the transdermal delivery system is maintained at 25° C.±2° C./60% RH±5% RH.

5.3 Methods of Use

In one embodiment, disclosed herein is a method of treating attention deficit disorder and attention deficit/hyperactivity disorder comprising topically administering methylphenidate transdermal delivery system wherein the methylphenidate is present in an amount sufficient to achieve substantially zero order kinetics for delivery to the skin or mucosa of a patient in need thereof over a period of time at least about 2-4, 4-6, 6-8, 8-10, 10-12, 12-14, 14-16, 16-18, 18-20, 20-22, 22-24 hours, wherein the transdermal delivery system comprises a silicone layer and a drug-containing matrix layer.

In one embodiment, the methylphenidate is present in an amount sufficient to permit a delivery rate from about 5-10 mg, 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg/24 hours in order to achieve a therapeutically effective dose in a patient.

In one embodiment, the transdermal delivery system is formulated for daily application.

In one embodiment, disclosed herein is a method of treating attention deficit disorder (ADD) or attention deficit/hyperactivity disorder (ADHD), comprising transdermal administration of methylphenidate or its pharmaceutically acceptable salt to an individual with ADD or ADHD, at a rate in excess of 8 µg/cm$^2$/hr.

A method of treating attention deficit disorder (ADD) or attention deficit/hyperactivity disorder (ADHD), comprising transdermal administration of methylphenidate or its pharmaceutically acceptable salt to an individual with ADD or ADHD, at a rate in excess of 0.15 mg/kg/day.

5.4 Methods of Making the Transdermal Delivery System

Aspects of the present disclosure also include methods of producing the transdermal delivery system as disclosed above. In certain embodiment, a silicon adhesive layer is applied to a backing. In certain embodiments, the method includes forming a mixture by mixing methylphenidate or its pharmaceutically acceptable salt with one or more solvents, a rubber-based polymer to form a drug-containing matrix layer. In certain embodiments, the polymer is styrene-butadiene block copolymer comprising a hydrogenated synthetic hydrocarbon tackifier.

The silicone adhesive layer is first applied to the backing layer. The drug-containing matrix mixture is then applied to the silicone adhesive layer that is on top of the backing. The method may further include applying a release liner to the drug-containing matrix layer on the side that is opposite to the backing. In certain instances, the method of making the transdermal delivery system further includes placing the transdermal formulation into a package forming a kit. After placing the transdermal formulation into the package, the method may include sealing the package.

6. EXAMPLES

The following examples illustrate the synthesis and use of representative embodiments provided herein. These examples are not intended, nor are they to be construed, as limiting the scope of the claimed subject matter. It will be clear that the scope of subject matter may be practiced otherwise than as particularly described herein. Numerous modifications and variations of the subject matter are possible in view of the teachings herein and, therefore, are within the scope the claimed subject matter.

6.1 Materials and Methods

The transdermal system are manufactured according to known methodology such as blending (mixing) the polymer(s), drug, and other excipients with appropriate amount in the presence of an appropriate solvent, such as a volatile organic solvent, casting the wet blend onto a release liner, followed by evaporation of the volatile solvent(s) at appropriate drying conditions, laminating the adhesive layer, drug-containing matrix layer and the release liner onto a backing film.

The flux can be measured with a standard procedure using Franz diffusion cells, and the experiments were done on human cadaver skin. With Franz cells, in each Franz diffusion cell a disc (diameter of 25 mm) of human cadaver skin is placed on the receptor compartment. A transdermal delivery system is cut the same size as the skin and placed over the diffusion area in the center of the receptor. The donor compartment is then added and clamped to the assembly. At time 0, receptor medium solution 14 mL is added into the receptor compartment and the cell maintained at 32° C. Samples of the receptor compartment are taken periodically to determine the skin flux and analyzed by HPLC.

Flux Test

Flux tests were conducted using one embodiment of the transdermal delivery system. The following method was used in preparation and testing of the transdermal delivery system. First remove protective releasing liner of the patch and revealing the adhesive side of patch. Then attach the patch on to a human cadaver skin with adhesive side toward skin with gentle pressure against the back of the patch, to ensure firm adhesion. Next, secure the patch/skin complex between upper and lower chamber of Franz diffusion cell with skin side toward lower chamber, wherein the lower chamber is filled with buffer and heated in order to simulate conditions of the human body. By measuring methylphenidate concentration of the buffer in the lower chamber of the Franz diffusion cell, the permeated amount and flux of methylphenidate of the tested patch may be determined.

Flux data were obtained from two embodiments of the methylphenidate transdermal delivery system. In one embodiment, the transdermal delivery system comprises about 8% methylphenidate free base with no excipient whereas the second embodiment comprises about 8% methylphenidate with about 25% squalane. The transdermal delivery system achieved a flux of about 0.0248 mg/cm$^2$/hour whereas another embodiment, the transdermal delivery system achieved a flux of about 0.0530) mg/cm$^2$/hour. These results illustrate the efficacy of squalane in increasing flux of the methylphenidate transdermal delivery system. The results are presented in Table 1 below:

TABLE 1

| Formulation | Methylphenidate | Squalane | Cyclomethicone | Flux (mg/cm²/hour) |
|---|---|---|---|---|
| Ex 1 | 8% | 0% | 0% | 0.0248 |
| Ex 2 | 8% | 25% | 0% | 0.0530 |

As Table 1 illustrates, increase in the weight % of squalane resulted in increase in the flux rate. Notably, the transdermal delivery system comprising 25% weight percentage of squalene resulted in about 40% to about 50% increase in flux as compared to formulation 1 that does not comprise any excipient. Embodiments with cyclomethicone also resulted in higher flux than the embodiment without any excipient. An additional test was conducted to show that the methylphenidate transdermal delivery system is able to sustain delivery of methylphenidate at about zero order kinetics for over 8 hours of application.

In Vivo Pharmacokinetics Studies

The pharmacokinetics studies of a transdermal patch containing methylphenidate is assessed in 12 healthy volunteers. The transdermal system is apply to the healthy subjects topically on their hip for 9 hours. The blood samples were collected periodically. Methylphenidate concentrations were measured in blood plasma using a validated chromatographic method developed. This method was validated to demonstrate adequate sensitivity, specificity, linearity, recovery, accuracy and precision. The pharmacokinetics parameters such as $AUC_{0-t}$, $AUC_{0-\infty}$, $C_{max}$, $T_{max}$, $t_{1/2}$, were calculated using WinNonlin Pro 5.3 and above. The results are shown in Table 2.

TABLE 2

| Pharmacokinietcs Results | |
|---|---|
| Pharmacokinetic Parameters | Ex 8 |
| AUC0-t (h · ng/mL) | 129.2 ± 39.15 |
| AUC0-∞ (h · ng/mL) | 137.12 ± 39.99 |
| Cmax (ng/mL) | 15.37 ± 5.37 |
| Tmax (h) | 9.75 ± 0.62 |
| t½ (h) | 4.21 ± 0.67 |

Figure 4:
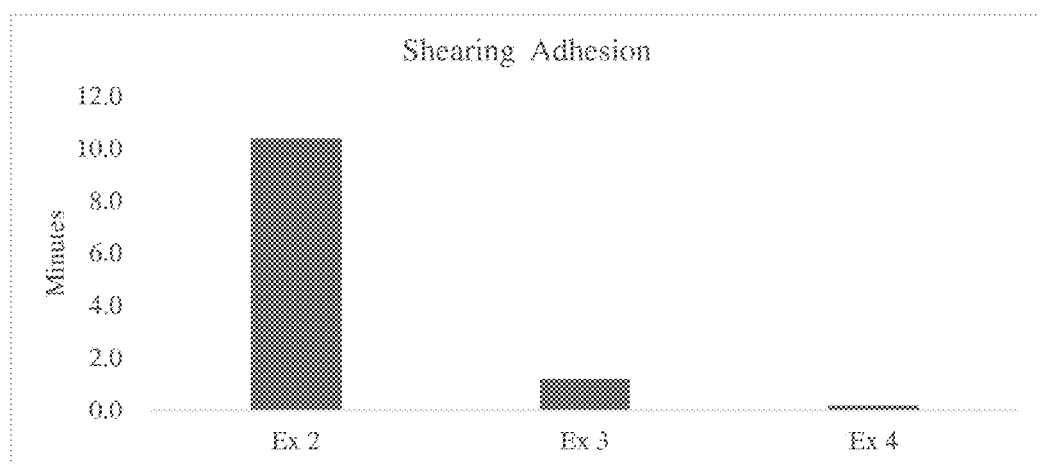
FIG. 4 shows a graph of shearing adhesion vs. different % drug loading. Generally, higher drug content lowers the shearing force.
Figure 5:
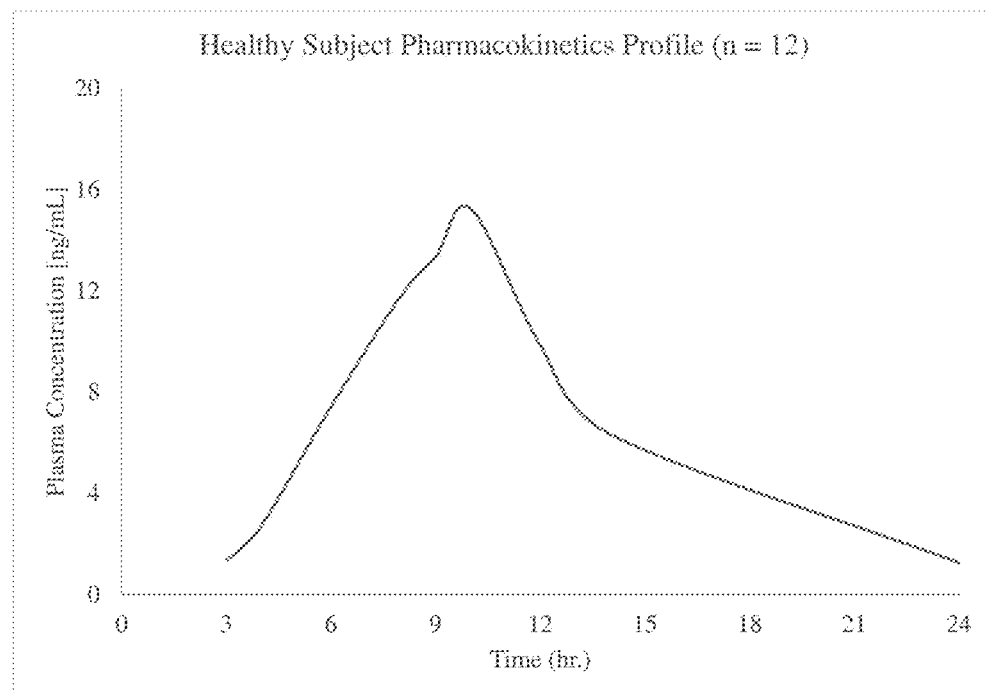
FIG. 5 shows healthy subject pharmacokinetics profile

Table 3 shows the relationship between % weight of methylphenidate and its effect on peel adhesion. Results are also shown in FIG. 4.

TABLE 3

| Ingredient | Example 3 % w/w | Example 4 % w/w | Example 5 % w/w | Example 6 % w/w |
|---|---|---|---|---|
| Methylphenidate | 0 | 8 | 12.5 | 17 |
| Limonene | 0 | 15 | 15 | 15 |
| Duro Tak 87-6911 | 100 | 77 | 72.5 | 68 |
| Peel adhesion (g/inch) | 2449.85 ± 26.24 | 1886.54 ± 98.49 | 2179.66 ± 102.24 | 2284.95 ± 115.75 |

| Example 7 Drug Composition Using Bilayer Adhesive Matrix | |
|---|---|
| Ingredient | % w/w |
| Methylphenidate | 17 |
| Duro Tak 87-6911 | 83 |
| (Blacking Layer without Drug) | |
| Silicone BIO PSA 7-4102 | 100 |
| Flux (µg/cm²/hr) | 13.12 |

| Example 8 Drug Composition Using Bilayer Adhesive Matrix | |
|---|---|
| Ingredient | % w/w |
| Methylphenidate | 17 |
| Duro Tak 87-6911 | 83 |
| (Blacking Layer without Drug) | |
| Silicone BIO PSA 7-4302 | 100 |
| Flux (µg/cm²/hr) | 20.67 |

| Example 9 Drug Composition Using Bilayer Adhesive Matrix | |
|---|---|
| Ingredient | % w/w |
| Methylphenidate | 17 |
| Duro Tak 87-6911 | 83 |
| (Blacking Layer without Drug) | |
| Silicone BIO PSA 7-4602 | 100 |
| Flux (µg/cm²/hr) | 14.90 |

| Example 10 Drug Composition Using Bilayer Adhesive Matrix | |
|---|---|
| Ingredient | % w/w |
| Methylphenidate | 17 |
| Duro mk 87-6911 | 83 |
| Flux (µg/cm²/hr) | 9.78 |

In Vitro Dissolution Studies

Figure 6:
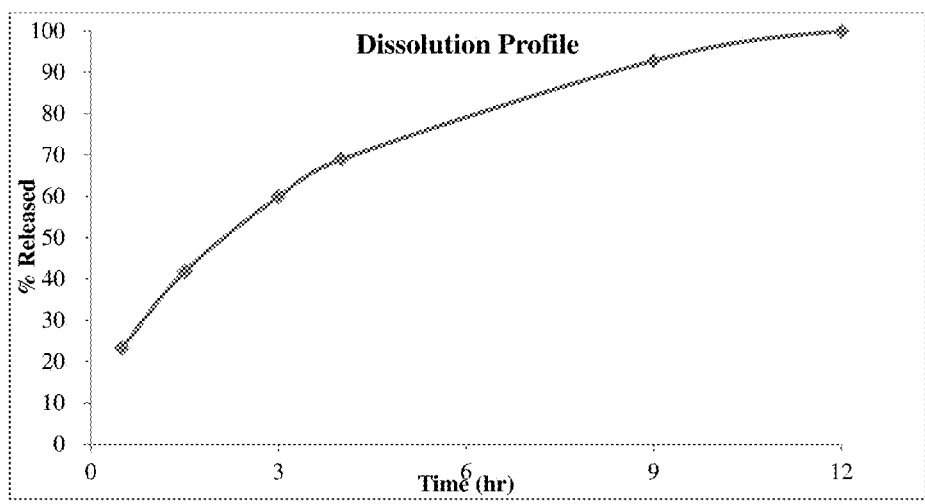
FIG. 6 shows in vitro dissolution profile of Example 8.
Figure 7:
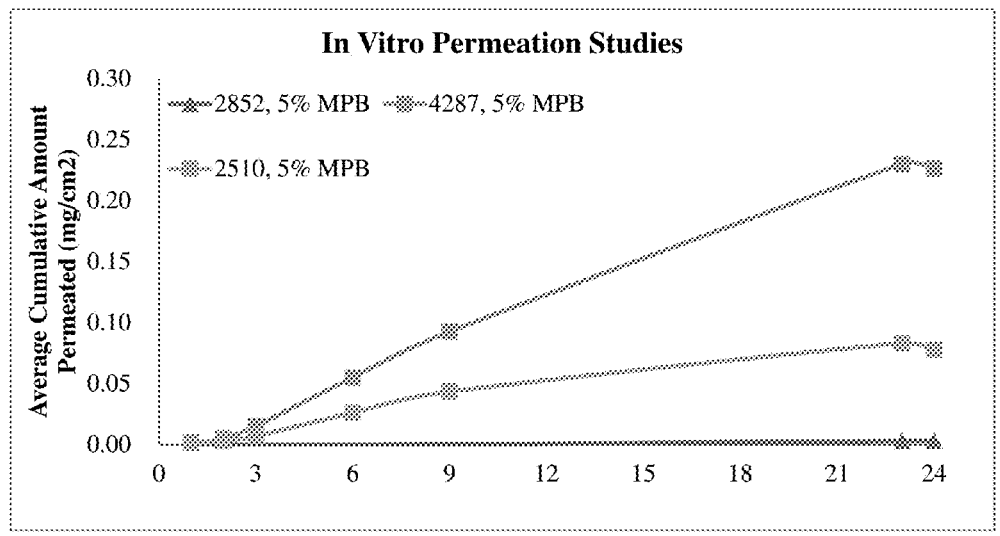
FIG. 7 shows in vitro permeation profile of accumulated amount from different acrylate adhesives.

Patch formulation composition as described in Example 10 were dissolved in dissolution buffer 0.01N HCl. Samples were collected at 0.5, 1.5, 3, 4, 9 and 12 hours. Methylphenidate content was determined by HPLC and the results are shown in FIG. 6.

It can be concluded that in less than 12 hours, there are more than 80% of the methylphenidate from Example 8 that will be released.

In one embodiment, the transdermal delivery system releases at least about 80% methylphenidate within 12 hours in an in vitro dissolution media at about pH1.2.

Stability Studies (Crystal Growth Observation and Impurity Analysis for Batch Compositions Using Silicone Adhesive and SBS Adhesive Products made from Example 8 and Example 10 were inspected for appearance, including color and crystal growth. They were then separately storage for 2 weeks at stress condition for as long as one month at accelerated aging conditions (40° C./75% RH.) and control room temperature conditions (25° C./60% RH.) and inspected. The results are set out below:

| Sample Name | Total Impurities (%) 60° C. 75% RH 1 weeks | Crystal Growth Observation | | |
|---|---|---|---|---|
| | | 25° C. 60% RH | 40° C. 75% RH | 60° C. 75% RH |
| Ex 8 | 1.50 | No color change | No color change | No color change |

-continued

| Sample Name | Total Impurities (%) 60° C. 75% RH 1 weeks | Crystal Growth Observation | | |
|---|---|---|---|---|
| | | 25° C. 60% RH | 40° C. 75% RH | 60° C. 75% RH |
| Ex 9 | 2.17 | Crystal Not Observed 1 Mo No color change Crystal Not Observed 1 Mo | Crystal Not Observed 1 Mo No color change Crystal Not Observed 1 Mo | Crystal Not Observed 1 Weeks No color change Crystal Not Observed 1 weeks |

Impurity is less than 5% and showed no crystal growth under all the conditions.

6.1.2. Formulations

Various adhesives were tested to determine the maximum amount of methylphenidate could be dissolved. The results are provided below:

| | Drug Composition in Duro Tak 87-6911 as Adhesive Matrix % w/w | |
|---|---|---|
| Ingredient | Example 11 | Example 12 |
| Methylphenidate | 20 | 40 |
| Duro Tak 87-6911 | q.s | q.s |
| Observation | soluble | Soluble |

| | Drug Composition in Acritical Adhesive Matrix % w/w | | |
|---|---|---|---|
| Ingredient | Example 13 | Example 14 | Example 15 |
| Methylphenidate | 5 | 5 | 5 |
| Duro Tak 387-4287 | q.s | | |
| Duro Tak 387-2852 | | q.s | |
| Duro Tak 387-2510 | | | q.s |
| Observation | soluble | soluble | Soluble |

| | Drug Composition in Silicone Adhesive Matrix % w/w | |
|---|---|---|
| Ingredient | Ex 16 | Ex 17 |
| Methylphenidate | 5 | 5 |
| Dow Corning 7-6302 | q.s | |
| Dow Corning 7-9900 | | q.s |
| Observation | Off white | incompatible |

6.1.5. Skin Permeation

Figure 2:
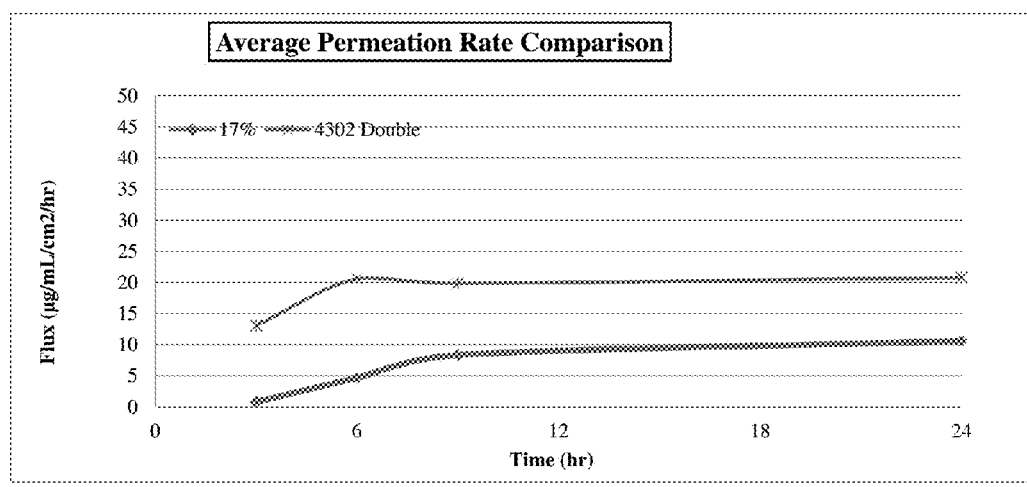
Figure 3:
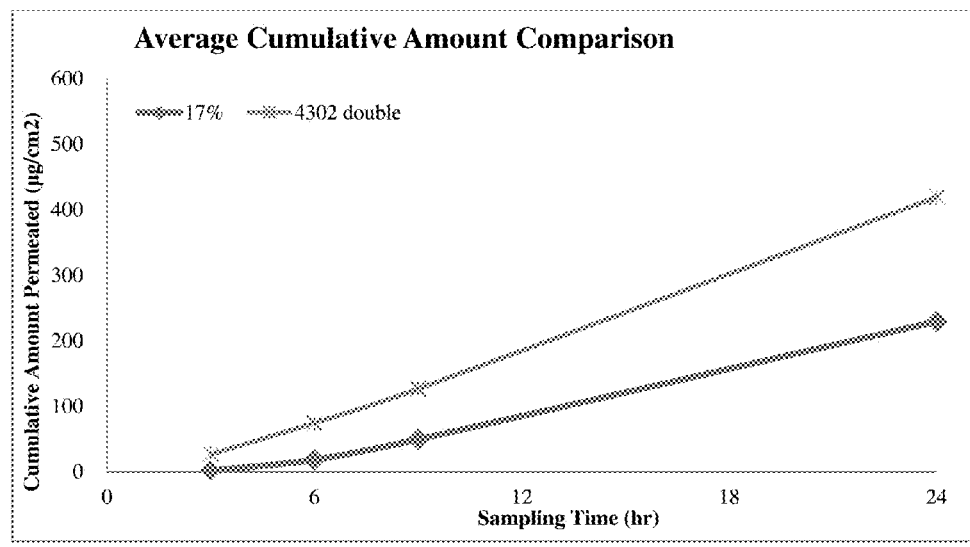
Figure 8:
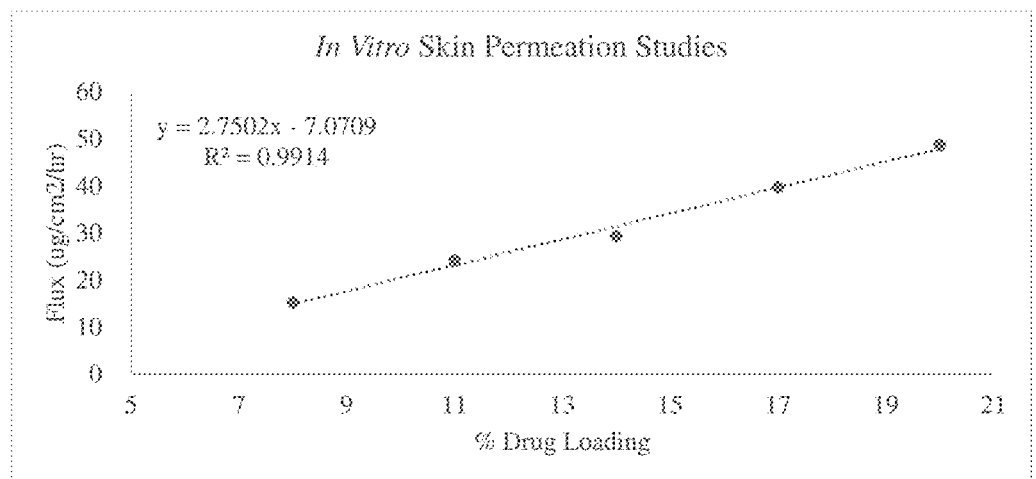
FIG. 8 shows linear relationship between drug loading and in vitro permeation rate for the bilayer formulations.

Skin permeation of various formulations were tested. The results are provided in FIGS. 2 and 3. Higher amount of the methylphenidate in the adhesives will increase the penetration. However, while methylphenidate is highly soluble in the Duro Tak 87-6911, when the amount of methylphenidate is over 40%, it was not able to coat as a film. As indicated that in FIG. 8 there is a linear relationship between the drug loading and permeation rate when the methylphenidate is less than 20% weight.

Examples 18-20 illustrate that the higher the drug loading, the higher the permeation rate.

| Example 18 Drug Composition Using Bilayer Adhesive Matrix | |
|---|---|
| Ingredient | % w/w |
| Methylphenidate | 8 |
| Duro Tak 87-6911 | 92 |
| (Blacking Layer without Drug) | |
| Silicone BIO PSA 7-4302 | 100 |

| Example 19 Drug Composition Using Bilayer Adhesive Matrix | |
|---|---|
| Ingredient | % w/w |
| Methylphenidate | 11 |
| Duro Tak 87-6911 | 89 |
| (Blacking Layer without Drug) | |
| Silicone BIO PSA 7-4302 | 100 |

| Example 20 Drug Composition Using Bilayer Adhesive Matrix | |
|---|---|
| Ingredient | % w/w |
| Methylphenidate | 20 |
| Duro Tak 87-6911 | 80 |
| (Blacking Layer without Drug) | |
| Silicone BIO PSA 7-4302 | 100 |

7. EXEMPLARY SYSTEMS AND METHODS ARE SET OUT IN THE FOLLOWING ITEMS

Item 1. A transdermal delivery system comprising: (i) a silicone adhesive layer; and (ii) a drug-containing matrix layer comprising: (a) methylphenidate or its pharmaceutically acceptable salt; and (b) a rubber-based polymer that comprises a hydrogenated synthetic hydrocarbon tackifier.

Item 2. The transdermal delivery system of the preceding item, wherein the rubber-based polymer is styrene-butadiene block copolymer rubber.

Item 3. The transdermal delivery system of anyone of the preceding items consisting essentially of a backing layer, the silicon adhesive layer, the drug-containing matrix layer, and a release liner.

Item 4. The transdermal delivery system of anyone of the preceding items, wherein the methylphenidate or its pharmaceutically acceptable salt is about 10 to about 20% by weight based on the total weight of the drug-containing matrix layer.

Item 5. The transdermal delivery system of anyone of the preceding items, wherein the methylphenidate or its pharmaceutically acceptable salt is about 12, about 15 or about 17% by weight based on the total weight of the drug-containing matrix layer.

Item 6. The transdermal delivery system of anyone of the preceding items, wherein the hydrogenated synthetic hydrocarbon tackifier is about 10-80% by weight based on the total weight of the drug-containing matrix layer.

Item 7. The transdermal delivery system of anyone of the preceding items wherein the silicone adhesive layer comprises 100% of silicone adhesive.

Item 8. The transdermal delivery system of anyone of the preceding items, wherein the drug-containing matrix layer further comprises an excipient.

Item 9. The transdermal delivery system of anyone of the preceding items, wherein the drug-containing matrix layer has a thickness from about 20 μm to about 48 m.

Item 10. The transdermal delivery system of anyone of the preceding items, wherein the size of a unit of the system has a dimension of about 2-60 cm$^2$.

Item 11. The transdermal delivery system of anyone of the preceding items, wherein the system has a flux of about 18-25 μg/cm$^2$/hr.

Item 12. The transdermal delivery system of anyone of the preceding items, wherein the system delivers methylphenidate and its pharmaceutically acceptable salts over a period of time of at least about 8-24 hours.

Item 13. The transdermal delivery system of anyone of the preceding items, wherein the methylphenidate or its pharmaceutically acceptable salt is about 15-19% by weight, wherein the styrene-butadiene block copolymer rubber comprises a hydrogenated synthetic hydrocarbon tackifier which is about 81-85% by weight based on the total weight of the drug-containing matrix layer.

Item 14. The transdermal delivery system of anyone of the preceding items, wherein the styrene-butadiene-styrene block copolymer comprises a hydrogenated synthetic hydrocarbon tackifier which is about 30-60% by weight based on the total weight of the drug-containing matrix layer.

Item 15. The transdermal delivery system of anyone of the preceding items, wherein the silicone layer increases flux by about 50-80% as compared to a control transdermal delivery system without the silicone layer.

Item 16. The transdermal delivery system of anyone of the preceding items, wherein the excipient does not degrade the methylphenidate or its pharmaceutically acceptable salt.

Item 17. The transdermal delivery system of anyone of the preceding items, wherein the drug-containing matrix layer further comprises a permeation enhancer.

Item 18. The transdermal delivery system of anyone of the preceding items, wherein the permeation enhancer comprises about 5% to about 25% of the total weight of the drug-containing matrix layer.

Item 19. The transdermal delivery system of anyone of the preceding items wherein the transdermal delivery system delivers the methylphenidate or its salts with substantially zero-order kinetics.

Item 20. The transdermal delivery system of anyone of the preceding items wherein the methylphenidate or its pharmaceutically acceptable salt comprises less than 5% of impurities.

Item 21. The transdermal delivery system of anyone of the preceding items wherein the transdermal delivery system has a shelf-life of at least 2 years at room temperature.

Item 22. The transdermal delivery system of anyone of the preceding items wherein the drug-containing matrix layer is color-stable and lacks crystal growth of methylphenidate or its pharmaceutically acceptable salt over an extended storage period of at least 2 years.

Item 23. The transdermal delivery system of anyone of the preceding items wherein the transdermal delivery system releases at least about 20-60% methylphenidate within 12 hours after administration to a subject.

Item 24. The transdermal delivery system of anyone of the preceding items wherein the transdermal delivery system releases at least about 30% methylphenidate within 12 hours after administration to a subject.

Item 25. The transdermal delivery system of anyone of the preceding items wherein the transdermal delivery system releases at least about 80% methylphenidate within 12 hours in the in vitro dissolution media at about pH 1.2.

Item 26. The transdermal delivery system of anyone of the preceding items wherein the transdermal delivery system has a flux rate ranging from about 6 μg/cm$^2$/hr-100 μg/cm$^2$/hr between 2-18 hours after treatment is initiated.

Item 27. A method of treating attention deficit disorder, attention deficit/hyperactivity disorder, postural orthostatic tachycardia syndrome or narcolepsy comprising topically administering methylphenidate and its pharmaceutically acceptable salts in a transdermal delivery system wherein the methylphenidate is present in an amount sufficient to achieve substantially zero order kinetics for delivery to the skin or mucosa of a patient in need thereof over a period of time at least 18 hours, wherein the transdermal delivery system comprises a silicone adhesive layer, a drug-containing matrix layer comprising a rubber-based polymer that comprises a hydrogenated synthetic hydrocarbon tackifier.

Item 28. A method of making the transdermal delivery system of preceding items 1 to 26 comprising the steps of:
(a) dissolving a desired amount of methylphenidate with a rubber-based polymer comprising a hydrogenated synthetic hydrocarbon tackifier to form a mixture;
(b) deaerating the mixture;
(c) laminating a silicon layer onto a supportive backing layer;
(d) laminating the mixture onto the silicon layer to form a wet film;
(e) drying the wet film to form a dry film;
(f) laminating the dry film with a releasing liner; and
(g) optionally cropping the dry film into a desired dimension.

The disclosure is not to be limited in scope by the specific embodiments described herein. Indeed, various modifications of the invention in addition to those described will become apparent to those skilled in the art from the foregoing description and accompanying figures. Such modifications are intended to fall within the scope of the appended claims. In fact, all the individual embodiments can be combined with one or more individual embodiments that are disclosed herein.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A transdermal delivery system comprising:
   (i) a silicone adhesive layer; and
   (ii) a drug-containing matrix layer comprising: (a) methylphenidate or its pharmaceutically acceptable salt; and (b) a rubber-based polymer that comprises a hydrogenated synthetic hydrocarbon tackifier, wherein the transdermal delivery system has a flux rate ranging from about 6 μg/cm$^2$/hr-100 μg/cm$^2$/hr between 2-18 hours after treatment is initiated.

2. The transdermal delivery system of claim 1, wherein the rubber-based polymer is styrene-butadiene block copolymer rubber.

3. The transdermal delivery system of claim 2, wherein the methylphenidate or its pharmaceutically acceptable salt is about 15-19% by weight based on the total weight of the drug-containing matrix layer, wherein the styrene-butadiene block copolymer rubber comprises a hydrogenated synthetic hydrocarbon tackifier which is about 10-85% by weight based on the total weight of the drug-containing matrix layer.

4. The transdermal delivery system of claim 2, wherein the styrene-butadiene block copolymer comprises a hydrogenated synthetic hydrocarbon tackifier which is about 60-85% by weight based on the total weight of the drug-containing matrix layer.

5. The transdermal delivery system of claim 1 consisting essentially of a backing layer, the silicone adhesive layer, the drug-containing matrix layer, and a release liner.

6. The transdermal delivery system of claim 1, wherein the methylphenidate or its pharmaceutically acceptable salt is about 10 to about 20% by weight based on the total weight of the drug-containing matrix layer.

7. The transdermal delivery system of claim 1, wherein the methylphenidate or its pharmaceutically acceptable salt is about 12, about 15 or about 17% by weight based on the total weight of the drug-containing matrix layer.

8. The transdermal delivery system of claim 1, wherein the hydrogenated synthetic hydrocarbon tackifier is about 10-80% by weight based on the total weight of the drug-containing matrix layer.

9. The transdermal delivery system of claim 1 wherein the silicone adhesive layer comprises 100% of silicone adhesive.

10. The transdermal delivery system of claim 1, wherein the drug-containing matrix layer further comprises an excipient.

11. The transdermal delivery system of claim 10 wherein the excipient does not degrade the methylphenidate or its pharmaceutically acceptable salt.

12. The transdermal delivery system of claim 1, wherein the drug-containing matrix layer has a thickness from about 20 μm to about 48 μm.

13. The transdermal delivery system of claim 1, wherein the size of a unit of the system has a dimension of about 2-60 cm².

14. The transdermal delivery system of claim 1, wherein the system has a flux of about 18-25 μg/cm²/hr.

15. The transdermal delivery system of claim 1, wherein the system delivers methylphenidate and its pharmaceutically acceptable salts over a period of time of at least about 8-24 hours.

16. The transdermal delivery system of claim 1, wherein the silicone layer increases flux by about 50-80% as compared to a control transdermal delivery system without the silicone layer.

17. The transdermal delivery system of claim 1, wherein the drug-containing matrix layer further comprises a permeation enhancer.

18. The transdermal delivery system of claim 17, wherein the permeation enhancer comprises about 5% to about 25% of the total weight of the drug-containing matrix layer.

19. The transdermal delivery system of claim 1 wherein the transdermal delivery system delivers the methylphenidate or its salts with substantially zero-order kinetics.

20. The transdermal delivery system of claim 1 wherein the methylphenidate or its pharmaceutically acceptable salt comprises less than 5% of impurities.

21. The transdermal delivery system of claim 1 wherein the drug-containing matrix layer is color-stable and lacks crystal growth of methylphenidate or its pharmaceutically acceptable salt over an extended storage period of at least 2 years at room temperature.

22. The transdermal delivery system of claim 1 wherein the transdermal delivery system releases at least about 20-60% methylphenidate within 12 hours after administration to a subject.

23. The transdermal delivery system of claim 22 wherein the transdermal delivery system releases at least about 30% methylphenidate within 12 hours after administration to a subject.

24. The transdermal delivery system of claim 1 wherein the transdermal delivery system releases at least about 80% methylphenidate within 12 hours in an in vitro dissolution media at about pH1.2.

25. A method of making the transdermal delivery system of claim 1 comprising the steps of:
  (a) dissolving a desired amount of methylphenidate with a rubber-based polymer comprising a hydrogenated synthetic hydrocarbon tackifier to form a mixture;
  (b) deaerating the mixture;
  (c) laminating a silicone layer onto a supportive backing layer;
  (d) laminating the mixture onto the silicon layer to form a wet film;
  (e) drying the wet film to form a dry film;
  (f) laminating the dry film with a releasing liner; and
  (g) optionally cropping the dry film into a desired dimension.

* * * * *